(12) United States Patent
Augostino

(10) Patent No.: US 10,098,671 B2
(45) Date of Patent: Oct. 16, 2018

(54) ADJACENT LEVEL FACET ARTHOROPLASTY DEVICES, SPINE STABILIZATION SYSTEMS, AND METHODS

(71) Applicant: GLOBUS MEDICAL, INC., Audubon, PA (US)

(72) Inventor: Teena M. Augostino, Redmond, WA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 42 days.

(21) Appl. No.: 15/071,328

(22) Filed: Mar. 16, 2016

(65) Prior Publication Data
US 2016/0262804 A1 Sep. 15, 2016

Related U.S. Application Data

(63) Continuation of application No. 13/771,881, filed on Feb. 20, 2013, now Pat. No. 9,320,547, which is a
(Continued)

(51) Int. Cl.
*A61B 17/70* (2006.01)
*A61F 2/44* (2006.01)
(Continued)

(52) U.S. Cl.
CPC ........ *A61B 17/7043* (2013.01); *A61B 17/705* (2013.01); *A61B 17/7049* (2013.01); *A61F 2/4405* (2013.01); *A61B 17/7064* (2013.01); *A61B 17/86* (2013.01); *A61B 2017/7073* (2013.01); *A61F 2002/3055* (2013.01); *A61F 2002/30242* (2013.01); *A61F 2002/30481* (2013.01); *A61F 2002/30507* (2013.01); *A61F 2002/30512* (2013.01); *A61F 2002/30523* (2013.01); *A61F 2002/30649* (2013.01); *A61F 2220/0025* (2013.01); *A61F 2230/0071* (2013.01)

(58) Field of Classification Search
CPC ..................... A61B 17/7049; A61B 17/7064
See application file for complete search history.

(56) References Cited

U.S. PATENT DOCUMENTS

| 6,241,730 B1 * | 6/2001 | Alby | ................. | A61B 17/7007 403/120 |
| 7,686,833 B1 * | 3/2010 | Muhanna | ........... | A61B 17/7005 606/257 |

(Continued)

*Primary Examiner* — Jan Christopher Merene

(57) ABSTRACT

The invention discloses an implantable facet arthroplasty device suitable for treating adjacent level disease. The device is designed for implantation between a first vertebra and a second vertebra. Components of the device include: a crossbar; a first component having a first attachment mechanism adapted to attach to a first location of a spinal fusion device attached to a first vertebra and a second attachment mechanism adapted to attach to the crossbar; and a second component having a second attachment mechanism adapted to attach to a second location of a spinal fusion device attached to the first vertebra and a second attachment mechanism adapted to attach to the crossbar. The first component articulates relative to the second component and the first vertebra articulates relative to the device itself.

5 Claims, 20 Drawing Sheets

Related U.S. Application Data continuation of application No. 11/206,662, filed on Aug. 17, 2005, now Pat. No. 8,398,681.

(60) Provisional application No. 60/602,826, filed on Aug. 18, 2004, provisional application No. 60/691,946, filed on Jun. 17, 2005.

(51) Int. Cl.
  *A61B 17/86* (2006.01)
  *A61F 2/30* (2006.01)

(56) References Cited

U.S. PATENT DOCUMENTS

| | | | | |
|---|---|---|---|---|
| 2002/0169448 | A1* | 11/2002 | Vanacker | A61B 17/6425 606/60 |
| 2004/0015172 | A1* | 1/2004 | Biedermann | A61B 17/864 606/304 |
| 2004/0122431 | A1* | 6/2004 | Biedermann | A61B 17/864 606/62 |
| 2005/0038432 | A1* | 2/2005 | Shaolian | A61B 17/1671 606/86 A |
| 2005/0080416 | A1* | 4/2005 | Ryan | A61B 17/7049 606/252 |
| 2005/0113927 | A1* | 5/2005 | Malek | A61B 17/7008 623/17.16 |

* cited by examiner

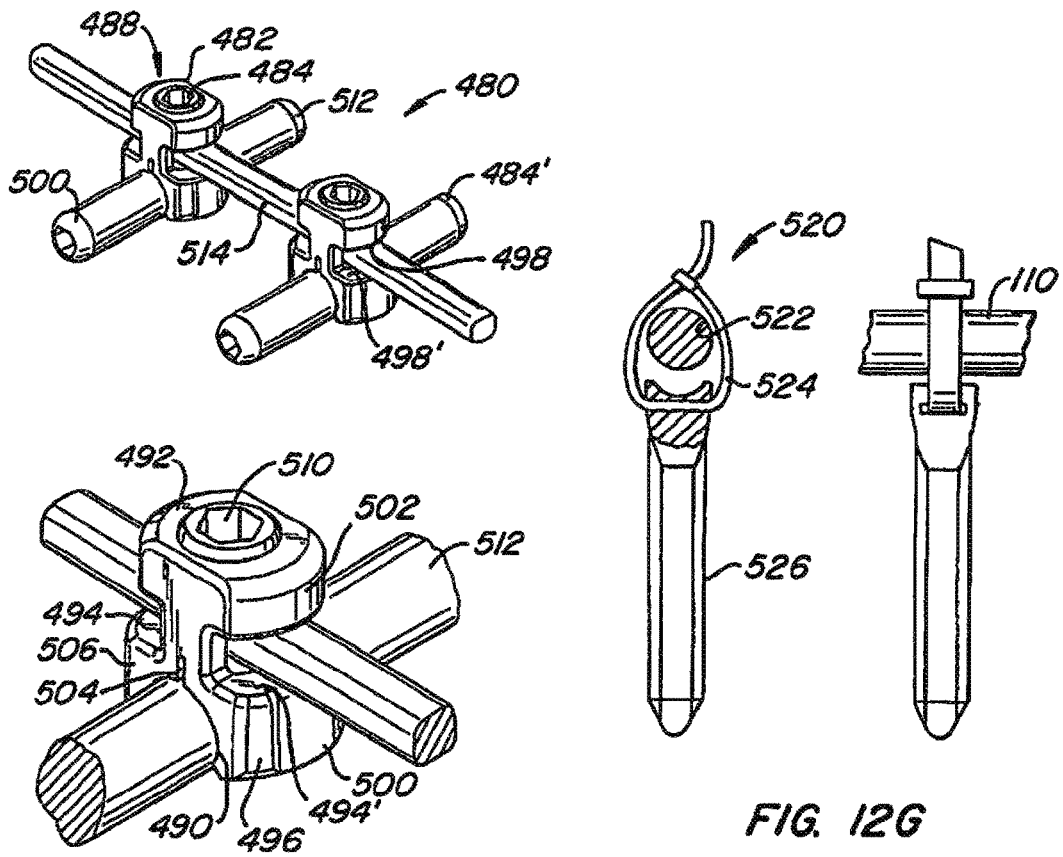
FIG. 12F
FIG. 12G
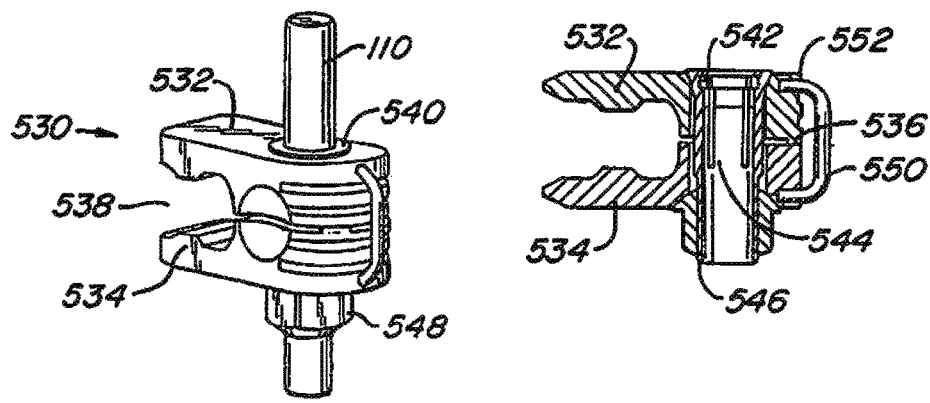
FIG. 12H

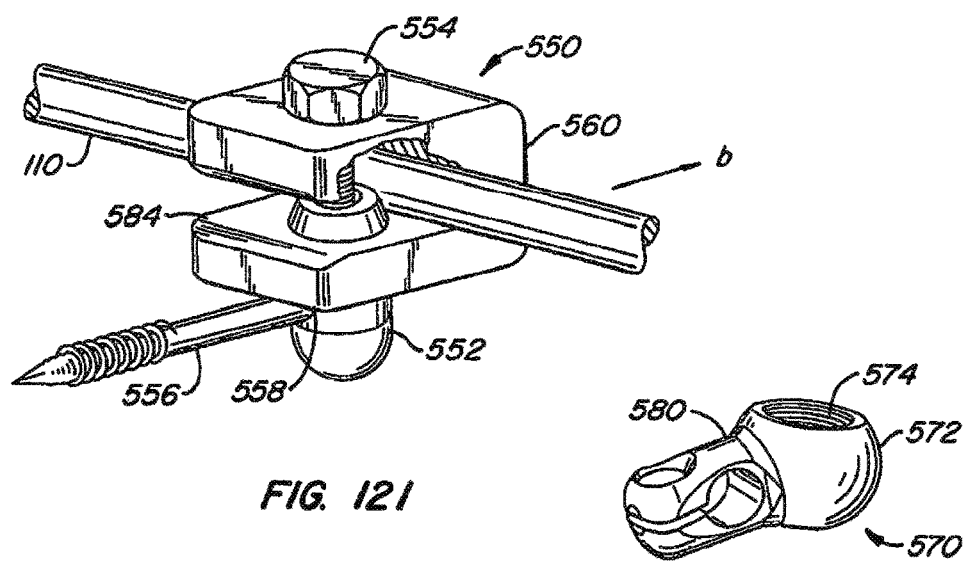
FIG. 12I
FIG. 12J
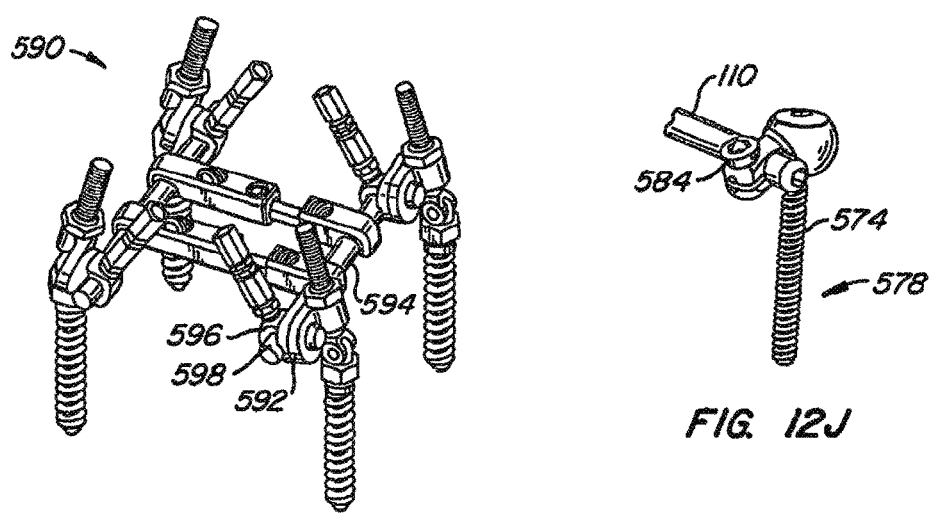
FIG. 12K

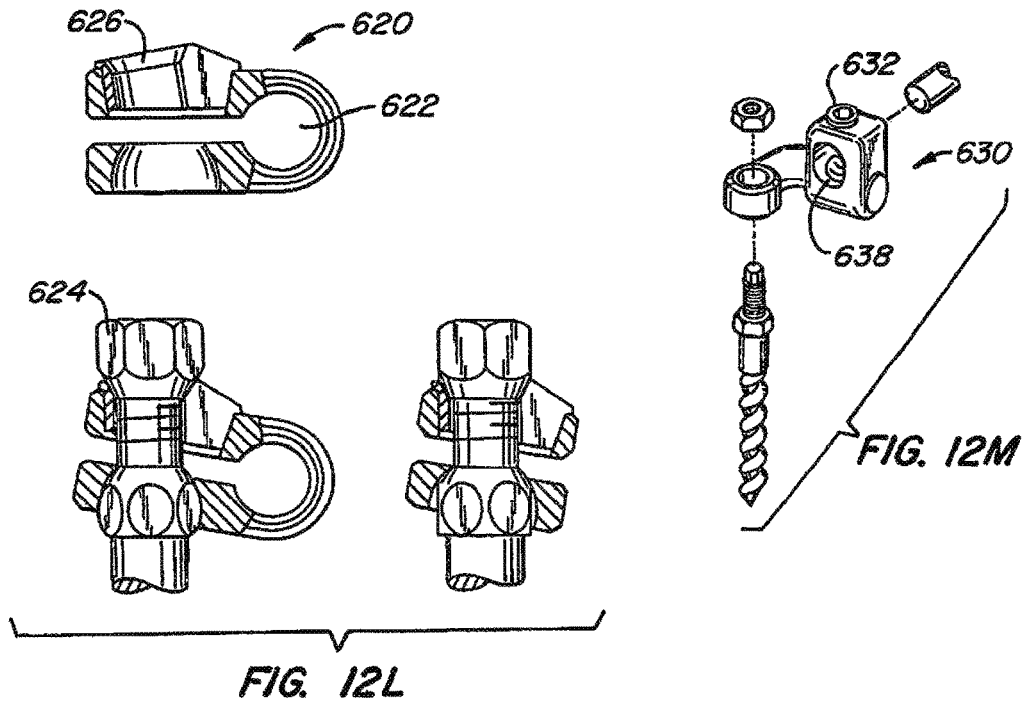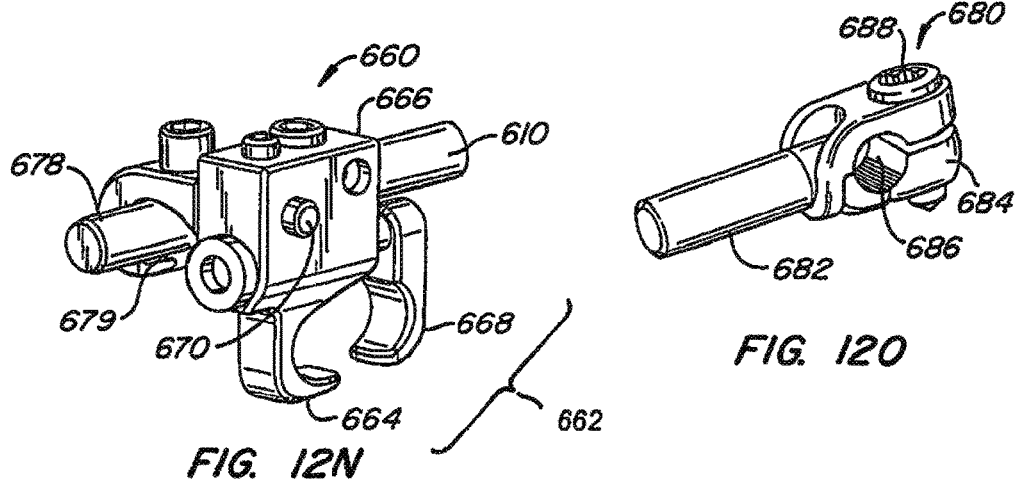

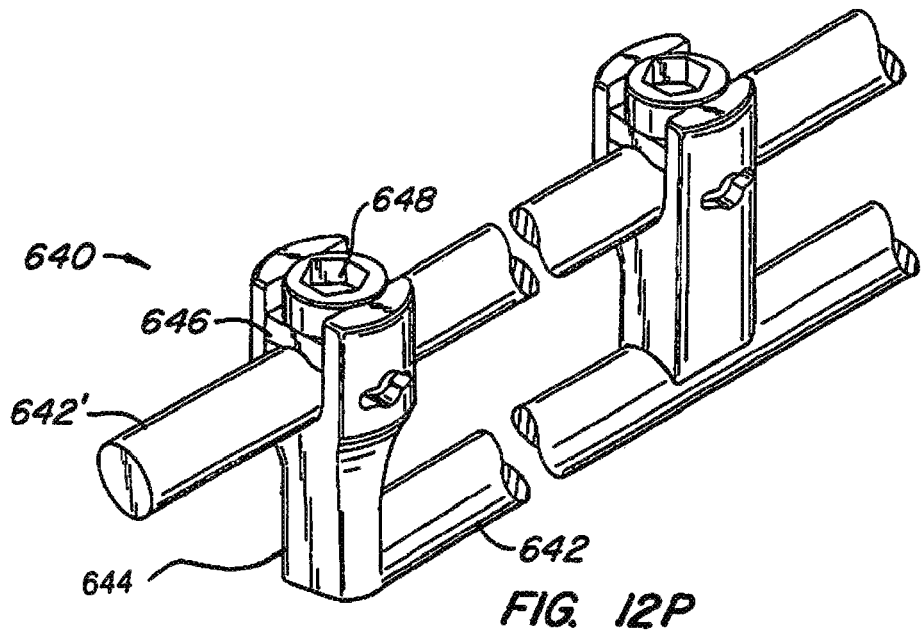
FIG. 12P
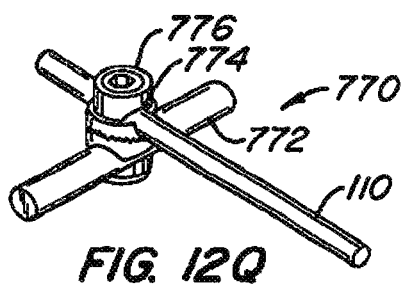
FIG. 12Q
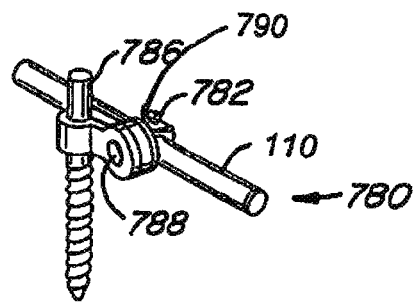
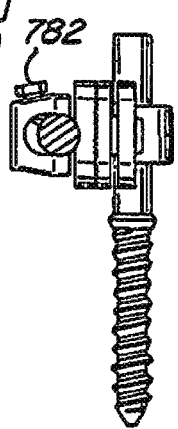
FIG. 12R
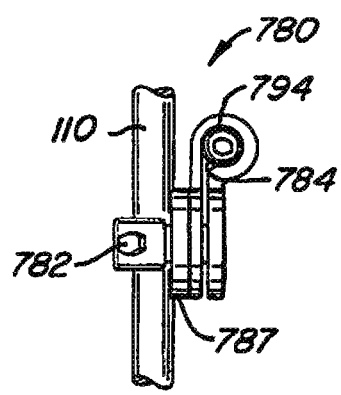

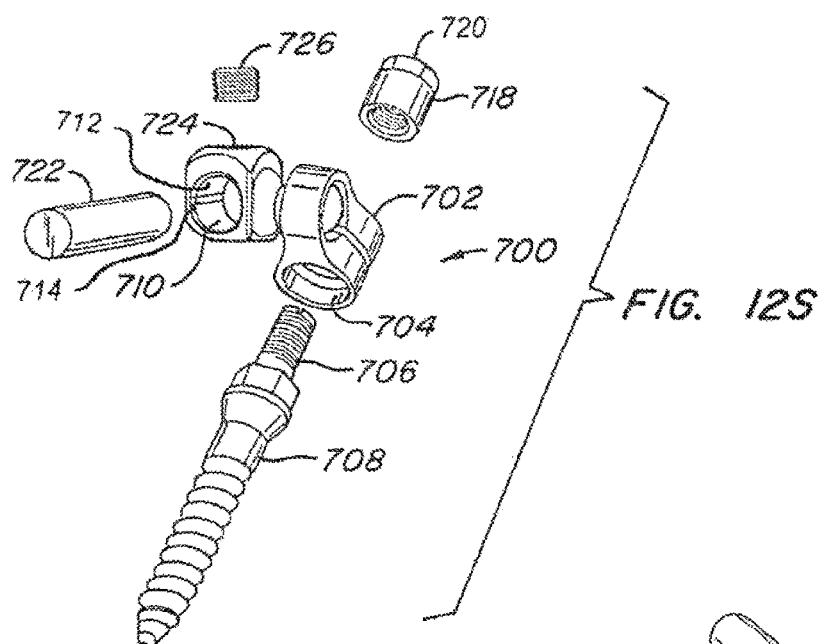
FIG. 12S
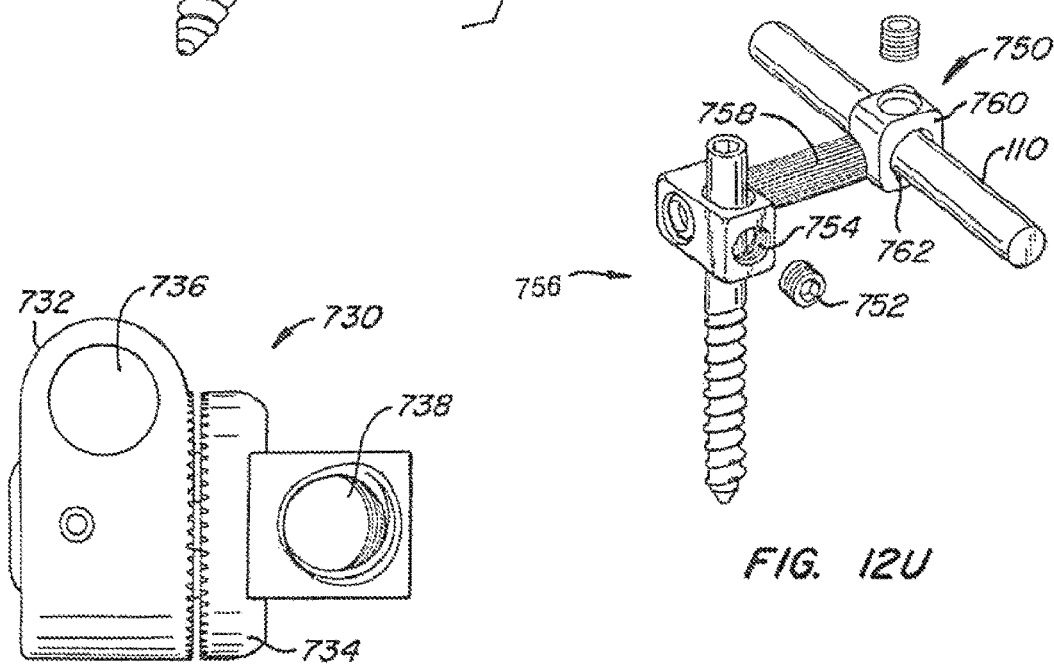
FIG. 12T
FIG. 12U

ADJACENT LEVEL FACET ARTHOROPLASTY DEVICES, SPINE STABILIZATION SYSTEMS, AND METHODS

CROSS-REFERENCE TO RELATED APPLICATIONS

This application is a continuation of U.S. patent application Ser. No. 13/771,881, now U.S. Pat. No. 9,320,547, filed Feb. 20, 2013, which is a continuation of U.S. patent application Ser. No. 11/206,662, filed Aug. 17, 2005, now U.S. Pat. No. 8,398,681, which claims the benefit of U.S. Provisional Application No. 60/602,826, filed Aug. 18, 2004 and U.S. Provisional Application No. 60/691,946 filed Jun. 17, 2005, which are incorporated herein by reference in their entireties.

This application is related to the following U.S. patent applications: U.S. patent application Ser. No. 10/973,939, filed Oct. 25, 2004, now abandoned; and application U.S. patent application Ser. No. 10/973,834, filed Oct. 25, 2004, now issued as U.S. Pat. No. 7,608,104, which are also incorporated herein by reference in their entireties.

FIELD OF THE INVENTION

This invention relates to devices, including devices for replacing or restoring part of bone, systems and methods for treating spinal pathologies. The devices, systems and methods of the invention are designed to achieve spinal stabilization and facet replacement. The devices, systems and methods are also designed to achieve spine fusion at a portion of the spine in combination with spine stabilization adjacent the fused section.

BACKGROUND OF THE INVENTION

Back pain, particularly in the small of the back, or lumbosacral region (L4-S1) of the spine, is a common ailment. In many cases, the pain severely limits a person's functional ability and quality of life. Back pain interferes with work, routine daily activities, and recreation. It is estimated that Americans spend $50 billion each year on low back pain alone. It is the most common cause of job-related disability and a leading contributor to missed work.

Through disease or injury, the laminae, spinous process, articular processes, facets and/or facet capsule(s) of one or more vertebral bodies along with one or more intervertebral discs can become damaged which can result in a loss of proper alignment or loss of proper articulation of the vertebra. This damage can result in anatomical changes, loss of mobility, and pain or discomfort. For example, the vertebral facet joints can be damaged by traumatic injury or as a result of disease. Diseases damaging the spine and/or facets include osteoarthritis where the cartilage of joints is gradually worn away and the adjacent bone is remodeled, ankylosing spondylolysis (or rheumatoid arthritis) of the spine which can lead to spinal rigidity, and degenerative spondylolisthesis which results in a forward displacement of the lumbar vertebra on the sacrum. Damage to facet joints of the vertebral body often can also results in pressure on nerves, commonly referred to as "pinched" nerves, or nerve compression or impingement. The result is pain, misaligned anatomy, and a corresponding loss of mobility. Pressure on nerves can also occur without facet joint pathology, e.g., a herniated disc.

One conventional treatment of facet joint pathology is spine stabilization, also known as intervertebral stabilization. Intervertebral stabilization desirably controls, prevents or limits relative motion between the vertebrae, through the use of spinal hardware, removal of some or all of the intervertebral disc, fixation of the facet joints, bone graft/osteo-inductive/osteo-conductive material (with or without concurrent insertion of fusion cages) positioned between the vertebral bodies, and/or some combination thereof, resulting in the fixation of (or limiting the motion of) any number of adjacent vertebrae to stabilize and prevent/limit/control relative movement between those treated vertebrae. Stabilization of vertebral bodies can range from the insertion of motion limiting devices (such as intervertebral spacers, artificial ligaments and/or dynamic stabilization devices), through devices promoting arthrodesis (rod and screw systems, cable fixation systems, fusion cages, etc.), up to and including complete removal of some or all of a vertebral body from the spinal column (which may be due to extensive bone damage and/or tumorous growth inside the bone) and insertion of a vertebral body replacement (generally anchored into the adjacent upper and lower vertebral bodies). Various devices are known for fixing the spine and/or sacral bone adjacent the vertebra, as well as attaching devices used for fixation.

One common concern with existing spinal fusion techniques relates to the increased stresses experienced in vertebra adjacent to fused spinal levels. Where one or more functional spine units (a functional spinal unit comprising a pair of adjacent vertebrae and the intervertebral disc and facet joints there between) are fused (or motion is reduced or limited in some manner), the stresses and strains normally accommodated by that flexible unit (now fused or less flexible) are transferred (at least partially) to adjacent spinal units. Where these increased stresses begin to damage and/or degrade other spinal units—which can often occur in levels directly adjacent to the fused level(s)—the degradation is often called "adjacent-level disease" or adjacent segment disease. See, Kulkami, et al. "Accelerated spondylotic changes adjacent to the fused segment following central cervical corpectomy: magnetic resonance imaging study evidence" J. Neurosurg. 100 (1 Suppl Spine):2-6 (2004). Where an adjacent level degrades to the point of requiring surgical intervention, the affected/degraded spinal unit is generally fused (or motion is limited and/or controlled in some manner), further exacerbating the stresses experienced by the remaining unfused levels, and often resulting in multiple-level or "daisy chained" fusions to the spine over time. The spine can be fused using, for example, a spinal fixation system.

More recently, various treatments have been proposed and developed as alternatives to spinal fusion. Many of these treatments seek to restore (and/or maintain) some or all of the natural motion of the treated spinal unit, and can include intervertebral disc replacement, facet joint resurfacing, and facet joint replacement. Such solutions typically include devices that do not substantially impair spinal movement.

SUMMARY OF THE INVENTION

One aspect of the present invention includes the realization that there exists a need for a device for use on adjacent level facets that provides stabilization and protects the joint between two adjacent vertebra that are adjacent a fused or immobilized section of spine. There also exists a need for a system and/or device that can be attached at a spinal level already containing pedicle screws and/or other types of spinal instrumentation (including spinal fusion hardware such as rods and screws or other types of fusion and/or non-fusion spinal instrumentation) that relieves stress experienced by the unfused levels vertebra. Moreover, there exists a need for a facet joint replacement system having components that can be selectively attached to pre-existing spinal hardware (and/or can be used with limited modifications to the pre-existing spinal hardware or hardware added for treating various surgical conditions) as well as to various anatomical structures, including the lamina, pedicles and/or directly to the vertebral body or bodies (or some combination thereof, including simultaneous anchoring to spinal hardware and anatomical locations), as desired by the physician. Furthermore, there exists a need for a facet joint replacement system that can be implanted into vertebral levels which desirably reinforces and/or stabilizes the facet joint/intervertebral disc complex adjacent and/or in the vicinity of one or more fused spinal levels, to treat, reduce and/or prevent the onset of adjacent level disease in one or more non-fused spinal segments. Furthermore, there exists a need for a facet joint and intervertebral disk replacement system that can be used to revise or "take down" and already-fused spinal segment (or segments) and restore partial or full natural motion to that segment or segments. Furthermore, there exists a need for a facet joint replacement system that can be used to revise one or more fused levels of a multi-level arthrodesis, such that motion can be restored to at least a portion of the multi-level arthrodesis (i.e., one section of a four level arthrodesis can be "taken down", leaving two single-level arthrodeses separated by an articulating section containing the facet joint replacement system.

In an embodiment of the invention, an implantable facet arthroplasty device for association with a first vertebra and a second vertebra comprising: a crossbar; a first component having a first attachment mechanism adapted to attach to a first location of a spinal fusion device attached to a first vertebra and a second attachment mechanism adapted to engage the crossbar; and a second component having a second attachment mechanism adapted to attach to a second location of a spinal fusion device attached to the first vertebra and a second attachment mechanism adapted to engage the crossbar, wherein, the first component articulates relative to the second component; further wherein the first vertebra articulates relative to the facet arthroplasty device. The device can further comprise a first arm having a bone engaging end adapted to attach to a vertebral body at a first end and adapted to engage the crossbar at a second end. Additionally, the device can be configured to engage a caudal vertebral body or a cephalad vertebral body. Arthroplasty devices suitable for use with the invention include spinal fusion devices, such as devices that comprise a pair of elongaged members configured to extend along a portion of the spine adjacent a cephalad vertebra and a caudal vertebra and a plurality of attachment mechanisms for mounting the fusion device to the vertebra. In some embodiments, a second arm having a bone engaging end adapted to attach to a vertebral body at a first end and adapted to engage the crossbar at a second end. The second arm can be configured to engage a caudal vertebral body or a cephalad vertebral body. The first arm can be adapted to articulate relative to a second arm, in some embodiments.

In another embodiment of the invention, an implantable spinal restoration device comprising: an elongated member configured to extend along a portion of a length of a spine adjacent a cephalad vertebra and a caudal vertebra; an attachment mechanism adapted to attach the elongated member to a portion of the spine; a facet arthroplasty element; a support component having a first end and a second end sized to span a portion of the vertebral body and adapted to receive the facet arthroplasty element at the first end and the second end; and a connector adapted to connect the support component to the elongated member. Embodiments can also include an arm with a bone engaging end adapted to attach to a vertebra at a first end and adapted to attach to the support component at a second end. The arm can also be configured to engage a caudal vertebral body and/or a cephalad vertebral body. A second arm can also be provided having a first end adapted to engage a vertebral body at a first end and second end adapted to engage the crossbar. The first arm can be configured to articulates relative to the second arm. The support component can also be configured such that it is sized to span a portion of a vertebral body between a left lamina and a right lamina, such as a portion of a vertebral body between a left pedicle and a right pedicle. Thus, the support component can be further adapted to have an adjustable width. Additionally, the facet arthroplasty element is positioned relative to the support component to provide a symmetric anatomical solution. The facet arthroplasty element can also be positioned relative to the support component to provide an asymmetrical anatomical solution. Additionally, the ends of the support component are adapted to receive an opening in the facet arthroplasty element. The facet arthroplasty element can also be selected from a plurality of facet arthroplasty elements each having an opening with a different depth. Embodiments of the invention can provide for even distribution of the weight on the vertebral body.

A further embodiment of the invention includes an adaptable implantable spine stabilization device, comprising: a crossbar having a first end and a second end; a pair of vertebral engaging elements each having a bone engaging end and an end adapted to couple to the crossbar; and a pair of anchoring elements each having a first end having a surface adapted to receive a crossbar end and second end adapted to fix the anchoring element to a spinal fusion system. The device can further comprise an arm with a bone engaging end adapted to attach to a vertebra at a first end and adapted to attach to the support component at a second end. Further, the arm can be configured to engage a caudal vertebral body or a cephalad vertebral body. The second arm of an embodiment can be configured to engage a vertebral body at a first end and second end adapted to engage the crossbar. In such an instance, the first arm can be configured to articulate relative to the second arm. Further, the support component can be sized to span a portion of a vertebral body between a left lamina and a right lamina, or span a portion of a vertebral body between a left pedicle and a right pedicle. The support component may be further adapted to have an adjustable width. Embodiments of the invention can provide positioned relative to the support component to provide a symmetric anatomical solution, or an asymmetrical anatomical solution. The ends of the support component can also be adapted to receive an opening in the facet arthroplasty element. Additionally, each facet arthroplasty element can be selected from a plurality of facet arthroplasty elements each having an opening with a different depth. The weight can also be evenly distributed on the vertebral body using the support component.

An embodiment of the invention includes a method for revising spinal fusion surgery to provide support to adjacent vertebra comprising: accessing a spinal location having a spinal fusion device, comprising a pair of elongated members, attached adjacent a caudal vertebral body and a cephalad vertebral body; attaching a facet arthroplasty device comprising an articulating attachment mechanism adapted to receive a crossbar and an attachment mechanism adapted to connected to the elongated member of the spinal fusion device; and closing the wound. In a method of an embodiment, the vertebra adjacent the spinal fusion device are stabilized.

Yet another embodiment of the invention includes an implantable adjacent level arthroplasty device for implantation between a first vertebra and a second vertebra having a vertebra engaging a fusion device comprising: a crossbar; a first component having a first attachment mechanism adapted to attach to a first location of a spinal fusion device attached to a first vertebra and a second attachment mechanism adapted to attach to the crossbar; and a second component having a second attachment mechanism adapted to attach to a second location of a spinal fusion device attached to the first vertebra and a second attachment mechanism adapted to attach to the crossbar, wherein, the first component articulates relative to the second component; further wherein the first vertebra articulates relative to the facet arthroplasty device.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the claims that follow define the scope of the invention and that methods and structures within the scope of the claims and equivalents thereof are covered thereby.

The invention relates to implantable devices, including prosthesis suitable for implantation within the body to restore and/or augment connective tissue such as bone, and systems for treating spinal pathologies. The invention relates generally to implantable devices, apparatus or mechanisms that are suitable for implantation within a human body to restore, augment, and/or replace soft tissue and connective tissue, including bone and cartilage, and systems for treating spinal pathologies. In various embodiments, the implantable devices can include devices designed to replace missing, removed or resected body parts or structure. The implantable devices, apparatus or mechanisms are configured such that the devices can be formed from parts, elements or components which alone, or in combination, comprise the device. The implantable devices can also be configured such that one or more elements or components are formed integrally to achieve a desired physiological, operational or functional result such that the components complete the device. Functional results can include the surgical restoration and functional power of a joint, controlling, limiting or altering the functional power of a joint, and/or eliminating the functional power of a joint by preventing joint motion. Portions of the device can be configured to replace or augment existing anatomy and/or implanted devices, and/or be used in combination with resection or removal of existing anatomical structure.

Figure 1:
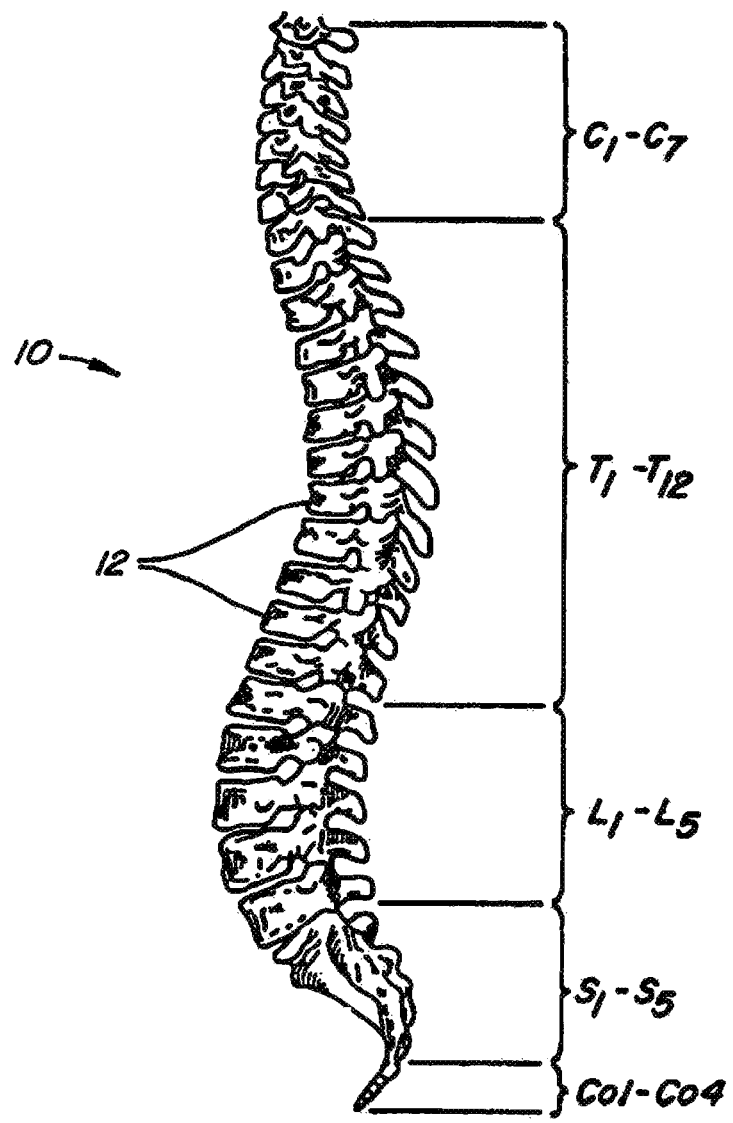
FIG. 1 is a lateral view of a normal human spinal column.

The devices of the invention are designed to interact with the human spinal column 10, as shown in FIG. 1, which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

Figure 2:
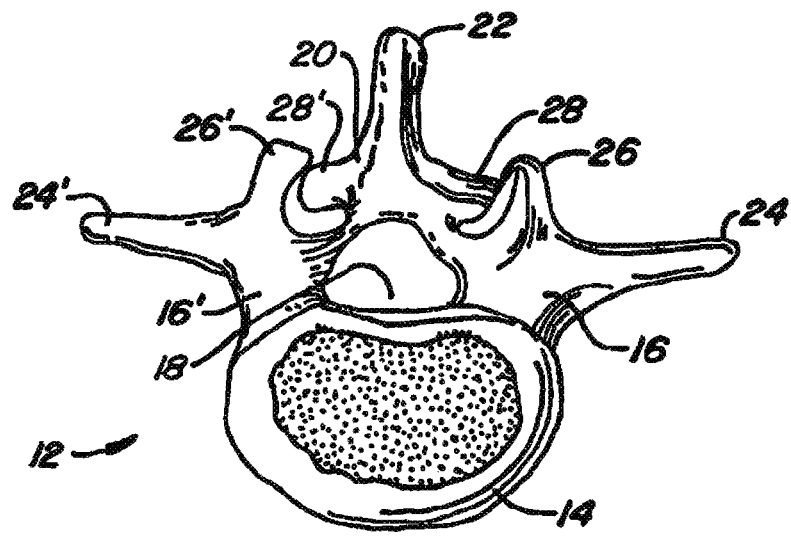
FIG. 2 is a superior view of a normal human lumbar vertebra.

An example of one vertebra is illustrated in FIG. 2 which depicts a superior plan view of a normal human lumbar vertebra 12. Although human lumbar vertebrae vary somewhat according to location, the vertebrae share many common features. Each vertebra 12 includes a vertebral body 14. Two short boney protrusions, the pedicles 16, 16', extend dorsally from each side of the vertebral body 14 to form a vertebral arch 18 which defines the vertebral foramen.

At the posterior end of each pedicle 16, the vertebral arch 18 flares out into broad plates of bone known as the laminae 20. The laminae 20 fuse with each other to form a spinous process 22. The spinous process 22 provides for muscle and ligamentous attachment. A smooth transition from the pedicles 16 to the laminae 20 is interrupted by the formation of a series of processes.

Two transverse processes 24, 24' thrust out laterally, one on each side, from the junction of the pedicle 16 with the lamina 20. The transverse processes 24, 24' serve as levers for the attachment of muscles to the vertebrae 12. Four articular processes, two superior 26, 26' and two inferior 28, 28', also rise from the junctions of the pedicles 16 and the laminae 20. The superior articular processes 26, 26' are sharp oval plates of bone rising upward on each side of the vertebrae, while the inferior processes 28, 28' are oval plates of bone that jut downward on each side. See also FIG. 4.

Figure 3:
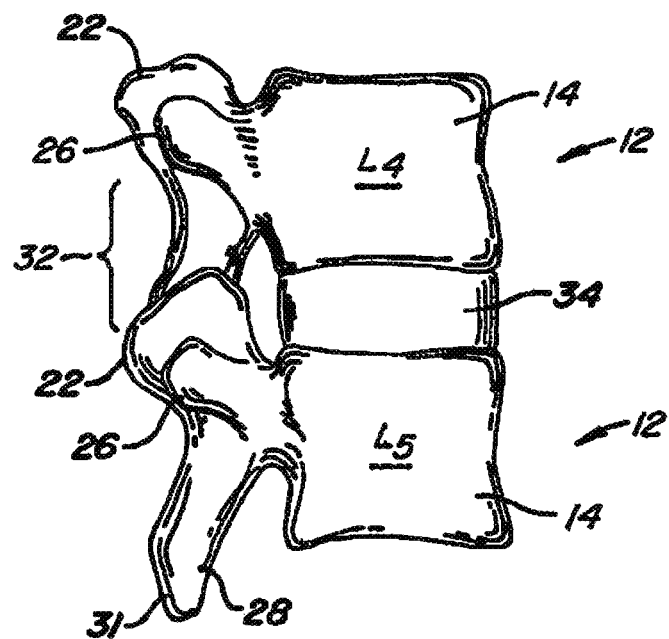
FIG. 3 is a lateral view of a functional spinal unit.

The superior and inferior articular processes 26 and 28 each have a natural bony structure known as a facet. The superior articular facet 30 faces medially upward, while the inferior articular facet 31 (see FIG. 3) faces laterally downward. When adjacent vertebrae 12 are aligned, the facets 30 and 31, capped with a smooth articular cartilage and encapsulated by ligaments, interlock to form a facet joint 32. The facet joints are apophyseal joints that have a loose capsule and a synovial lining.

As discussed, the facet joint 32 is composed of a superior facet and an inferior facet. The superior facet is formed by the vertebral level below the joint 32, and the inferior facet is formed in the vertebral level above the joint 32. For example, in the L4-L5 facet joint shown in FIG. 3, the superior facet of the joint 32 is formed by bony structure on the L5 vertebra (i.e., a superior articular surface and supporting bone 26 on the L5 vertebra), and the inferior facet of the joint 32 is formed by bony structure on the L4 vertebra (i.e., an inferior articular surface and supporting bone 28 on the L4 vertebra). The angle formed by a facet joint located between a superior facet and an inferior facet changes with respect to the midline depending upon the location of the vertebral body along the spine. The facet joints do not, in and of themselves, substantially support axial loads unless the spine is in an extension posture (lordosis). As would be appreciated by those of skill in the art, the orientation of the facet joint for a particular pair of vertebral bodies changes significantly from the thoracic to the lumbar spine to accommodate a joint's ability to resist flexion-extension, lateral bending, and rotation.

Figure 4:
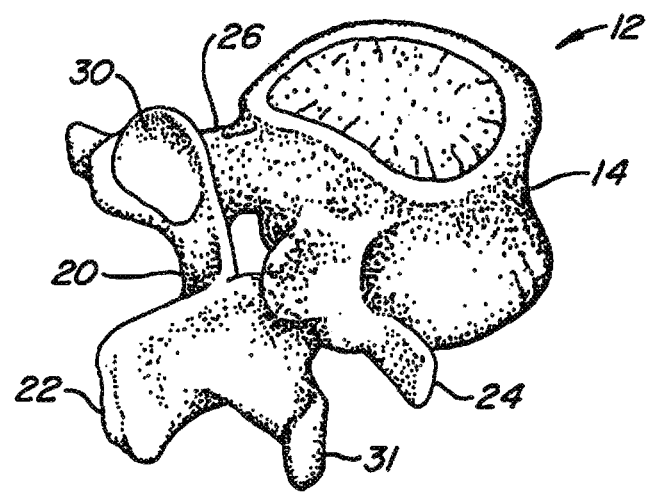
FIG. 4 is a posterolateral oblique view of a vertebrae.

An intervertebral disc 34 between each adjacent vertebra 12 (with stacked vertebral bodies shown as 14, 15 in FIG. 3) permits gliding movement between the vertebrae 12. The structure and alignment of the vertebrae 12 thus permit a range of movement of the vertebrae 12 relative to each other. FIG. 4 illustrates a posterolateral oblique view of a vertebrae 12, further illustrating the curved surface of the superior articular facet 30 and the protruding structure of the inferior facet 31 adapted to mate with the opposing superior articular facet. As discussed above, the position of the inferior facet 31 and superior facet 30 varies on a particular vertebral body to achieve the desired biomechanical behavior of a region of the spine.

Thus, the overall spine comprises a series of functional spinal units that are a motion segment consisting of two adjacent vertebral bodies, the intervertebral disc, associated ligaments, and facet joints. See, Posner, I, et al. A biomechanical analysis of the clinical stability of the lumbar and lumbrosacral spine. Spine 7:374-389 (1982).

As previously described, a natural facet joint, such as facet joint 32 (FIG. 3), has a superior facet 30 and an inferior facet 31. In anatomical terms, the superior facet of the joint is formed by the vertebral level below the joint, which can thus be called the "caudal" portion of the facet joint because it is anatomically closer to the tail bone or feet of the person. The inferior facet of the facet joint is formed by the vertebral level above the joint, which can be called the "cephalad" portion of the facet joint because it is anatomically closer to the head of the person. Thus, a device that, in use, replaces the caudal portion of a natural facet joint (i.e., the superior facet 30) can be referred to as a "caudal" device. Likewise, a device that, in use, replaces the cephalad portion of a natural facet joint (i.e., the inferior facet 31) can be referred to a "cephalad" device.

When the processes on one side of a vertebral body 14 are spaced differently from processes on the other side of the same vertebral body, components of the devices on each side would desirably be of differing sizes as well to account for anatomical difference that can occur between patients. Moreover, it can be difficult for a surgeon to determine the precise size and/or shape necessary for an implantable device until the surgical site has actually been prepared for receiving the device. In such case, the surgeon typically can quickly deploy a family of devices possessing differing sizes and/or shapes during the surgery. Thus, embodiments of the spinal devices of the present invention include modular designs that are either or both configurable and adaptable. Additionally, the various embodiments disclosed herein may also be formed into a "kit" or system of modular components that can be assembled in situ to create a patient specific solution. As will be appreciated by those of skill in the art, as imaging technology improves, and mechanisms for interpreting the images (e.g., software tools) improve, patient specific designs employing these concepts may be configured or manufactured prior to the surgery. Thus, it is within the scope of the invention to provide for patient specific devices with integrally formed components that are pre-configured.

A configurable modular device design, such as the one enabled by this invention, allows for individual components to be selected from a range of different sizes and utilized within a modular device. One example of size is to provide caudal and cephalad stems of various lengths. A modular implantable device design allows for individual components to be selected for different functional characteristics as well. One example of function is to provide stems having different surface features and/or textures to provide anti-rotation capability. Other examples of the configurability of modular implantable device of the present invention as described in greater detail below.

Implantable devices of the present invention are configurable such that the resulting implantable spinal device is selected and positioned to conform to a specific anatomy or desired surgical outcome. The adaptable aspect of embodiments of the present invention provide the surgeon with customization options during the implantation or revision procedure. It is the adaptability of the present device systems that also provides adjustment of the components during the implantation procedure to ensure optimal conformity to the desired anatomical orientation or surgical outcome. An adaptable modular device of the present invention allows for the adjustment of various component-to-component relationships. One example of a component-to-component relationship is the rotational angular relationship between a crossbar mount and the crossbar. Other examples of the adaptability of modular device of the present invention as described in greater detail below. Configurability may be thought of as the selection of a particular size of component that together with other component size selections results in a "custom fit" implantable device. Adaptability then can refer to the implantation and adjustment of the individual components within a range of positions in such a way as to fine tune the "custom fit" devices for an individual patient. The net result is that embodiments of the modular, configurable, adaptable spinal device and systems of the present invention allow the surgeon to alter the size, orientation, and relationship between the various components of the device to fit the particular needs of a patient during the actual surgical procedure.

Figure 5:
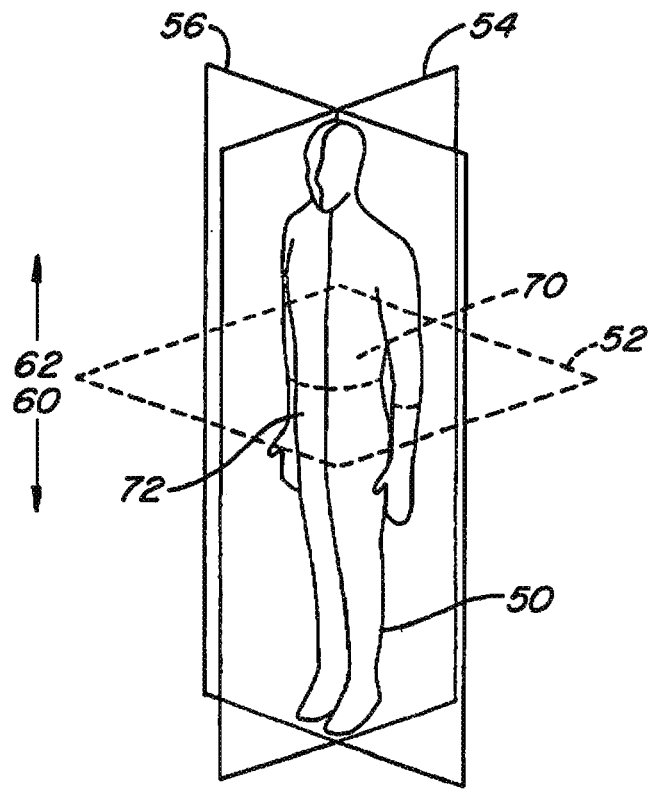
FIG. 5 is a perspective view of the anatomical planes of the human body.

In order to understand the configurability, adaptability, and operational aspects of the invention, it is helpful to understand the anatomical references of the body 50 with respect to which the position and operation of the devices, and components thereof, are described. There are three anatomical planes generally used in anatomy to describe the human body and structure within the human body: the axial plane 52, the sagittal plane 54 and the coronal plane 56 (see FIG. 5). Additionally, devices and the operation of devices are better understood with respect to the caudal 60 direction and/or the cephalad direction 62. Devices positioned within the body can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the spinal devices and systems of the present invention may be configurable and variable with respect to a single anatomical plane or with respect to two or more anatomical planes. For example, a component may be described as lying within and having adaptability or operability in relation to a single plane. For example, a stem may be positioned in a desired location relative to an axial plane and may be moveable between a number of adaptable positions or within a range of positions. Similarly, the various components can incorporate differing sizes and/or shapes in order to accommodate differing patient sizes and/or anticipated loads.

Figure 6A:
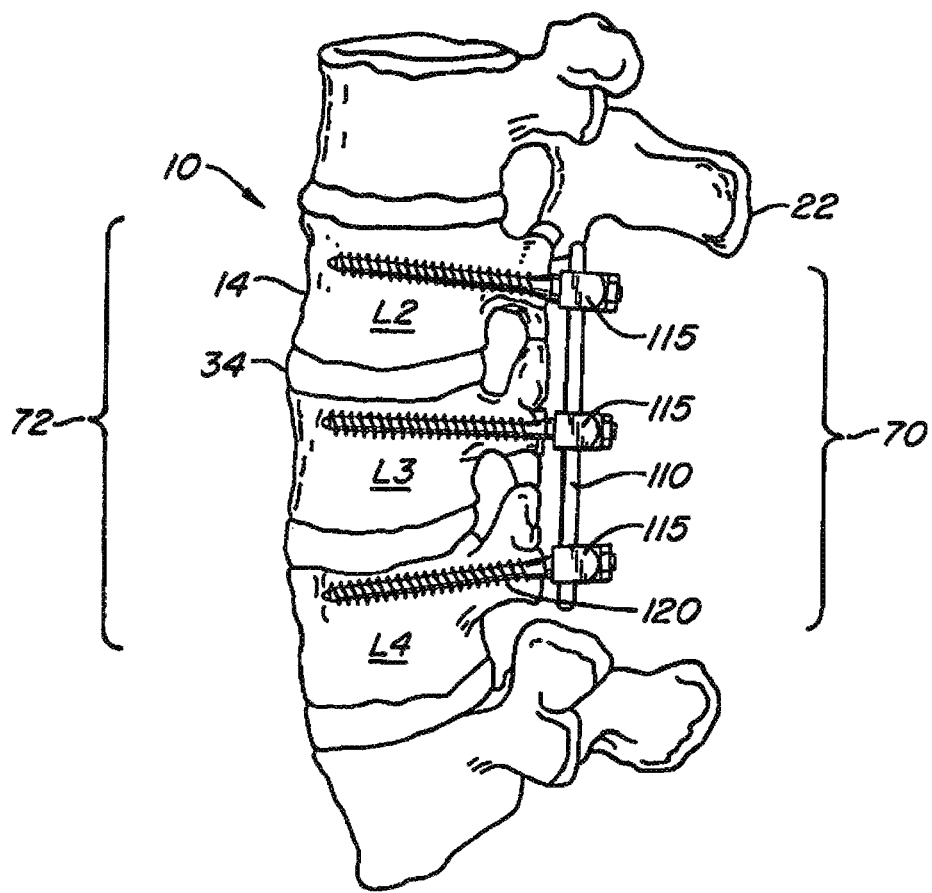
FIGS. 6A-B is a side view and a posterior view of a spinal fixation system.
Figure 6B:
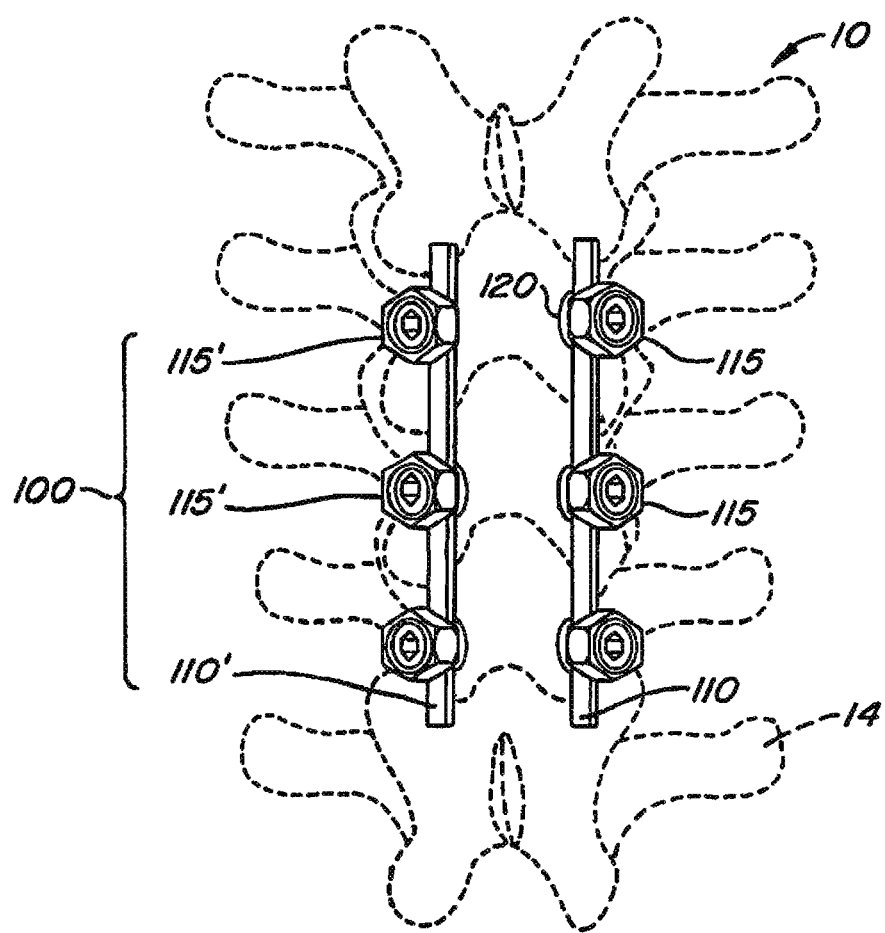

FIG. 6A is a view of a portion of the spine 10 having a spinal fusion implant 100 (such as the spinal fusion rod and screw system commercially available from SeaSpine corporation) from a side view positioned in the sagittal plane. The spinal implant 100 has a rod 110 which is anchored to the spine 10 with one or more anchors 120, such as bone screws that penetrate the vertebral body 14. The anchors 120 are fixed to the rod 110 via attachment mechanisms 115. FIG. 6B is a dorsal view of a portion of the spine 10 having a spinal implant 100. The spinal implant has a pair of rods 110, 110' which are anchored to the spine 10 with one or more anchors 120 (shown in FIG. 9A) fixed to the rods 110, 110' via attachment mechanisms 115.

Other spinal fixation systems can also be employed without departing from the scope of the invention. For example, systems using cables to stabilize the spine instead of rods can be employed. It is also contemplated the device can be used in combination with fixation systems positioned anteriorly, posteriorly, and laterally with respect to the spinal column.

Figure 7A:
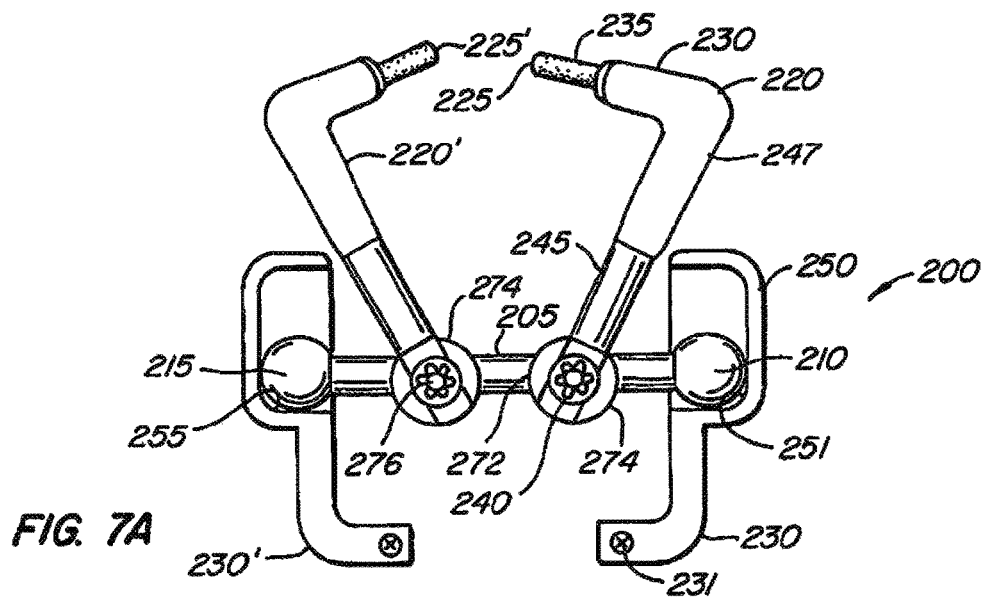
FIGS. 7A-C are views of one embodiment of an adjacent level facet arthroplasty device.

FIG. 7A is a posterior view of an anchorable facet replacement device 200 according to one embodiment of the present invention. The device 200 includes a crossbar 205, a pair of cephalad arms 220, 220' and a pair of connectors 230, 230'. In this exemplary embodiment, the facets 30 and 31 of the vertebral body are replaced by the cooperative operation of the crossbar 205, the cephalad arms 220, 220' and the adaptable crossbar mounts 276 that join the cephalad arms 220, 220' to the crossbar 205, interacting with the caudal device 250. The components of the cephalad implantable device 200 are designed to provide appropriate configurability and adaptability for the given disease state, patient specific anatomy and spinal level where the implant occurs.

The crossbar 205 has a first end 210 and a second end 215. The crossbar 205 can be formed from a two piece bar where the first end 210 is attached to a threaded male portion having threads (not shown). The crossbar second end 215 can be attached to a threaded female portion sized to receive the threads. It is contemplated that the threaded ends allow for the width of the crossbar to be adjusted to mate with the width between caudal bearings 250. Additional alternative embodiments of the crossbar 205 could include a series of solid crossbars of varying widths and/or thicknesses, or an adjustable crossbar having some form of locking or biasing mechanism (such as a spring-loaded tensioner or detent mechanism, etc.), as would be appreciated by those of skill in the art. Further, in an alternative embodiment, the end 210 can be configured to have a threaded male portion (instead of female portion) that fits within a female threaded portion of the crossbar 205 without departing from the scope of the invention.

A pair of cephalad arms 220 are also illustrated in the exemplary embodiment of the anchorable, adaptable implantable device 200 of the present invention. Each cephalad arm 220, 220' includes a bone engaging end 225, 225' and an end 240, 240' adapted to couple to the crossbar 205. The caudal end 240 adapted to engage the crossbar 205 includes an arm 245 and an elbow 247. The caudal end 240 is attached to the crossbar using the crossbar mount 276. The bone engaging cephalad end 225 includes a cephalad stem 230 and a distal tip 235. The cephalad stem 230 and the distal tip 235 are threaded or otherwise configured to engage the bone. Alternatively, the distal tip 235 could be formed integrally with the cephalad stem 230, of the same or a different material as the cephalad stem 230. The surface of the cephalad stem 230 can be a textured surface or any other modified surface such as, for example, a surface that assists or promotes bony in-growth.

The crossbar mount 275 is a connection structure to couple the cephalad prosthesis elements 220 to the crossbar 205. In the illustrated embodiment, the crossbar mount 275 includes a cephalad arm engaging portion 272, a crossbar engaging portion 274 and a fixation element 276. Embodiments of the crossbar mount 275 provide adaptability between the cephalad prosthesis elements 220 and the crossbar 205 and the loading characteristics of the crossbar ends 10, 215 and the caudal prosthesis 250.

A pair of caudal bearing elements 250 are also illustrated in the exemplary embodiment of the configurable and adaptable cephalad stabilization device 200 of the present invention. Each of the caudal bearing elements 250 includes a caudal cup 251. The caudal cup 251 includes a surface 255 adapted to receive a crossbar end and a surface to engage the caudal stem head engaging surface. Caudal connectors 230, 230' are provided to connect the implantable device 200 to the rods 110, 100' of the spinal implant 100 below the connection mechanism 115. The clamping mechanism 230 can attach to various portions of the spinal implant 100, including the rods 110, 110' or the connection mechanism 115. Other devices can be provided that are attached to all or part of the spinal implant 100, including cross-connectors and/or lateral rod connectors (not shown), or combinations thereof The clamping mechanisms 230, 230' can further be adapted to lock onto the spinal implant 100 by providing an additional connection mechanism 231 such as a bolt.

Figure 7B:
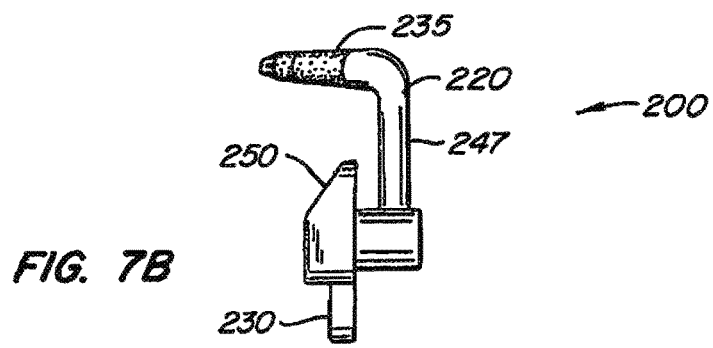
Figure 7C:
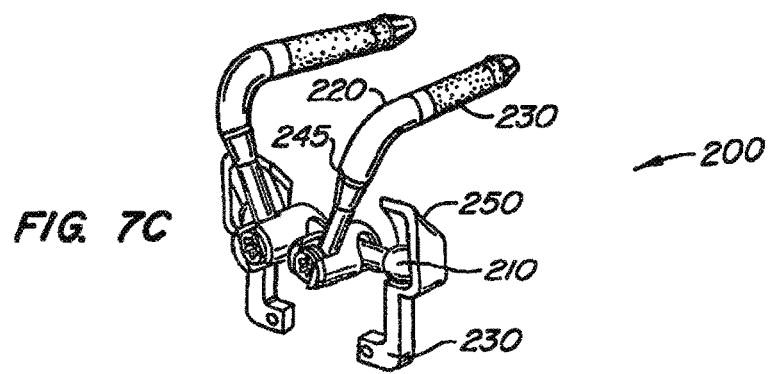

FIG. 7B illustrates the implantable device 200 from a side view; FIG. 7C illustrates the device 200 from a perspective view. As will be appreciated by those of skill in the art, in some instances, the device can be configured to function with only a single cephalad arm, thus allowing for a 3-point fixation mechanism, that in-turn is connected to the spinal fusion device. Where a 3-point fixation design is used, the cephalad arm 220 can be coupled to the cross-bar 205 such that the length of the arm 220 from the bone engaging end 225 to the cross-bar engaging end 240 crosses the midline of the vertebra along the vertical length of the sagittal 54 plane. Other attachment mechanisms can be provided without departing form the scope of the invention.

Figure 8A:
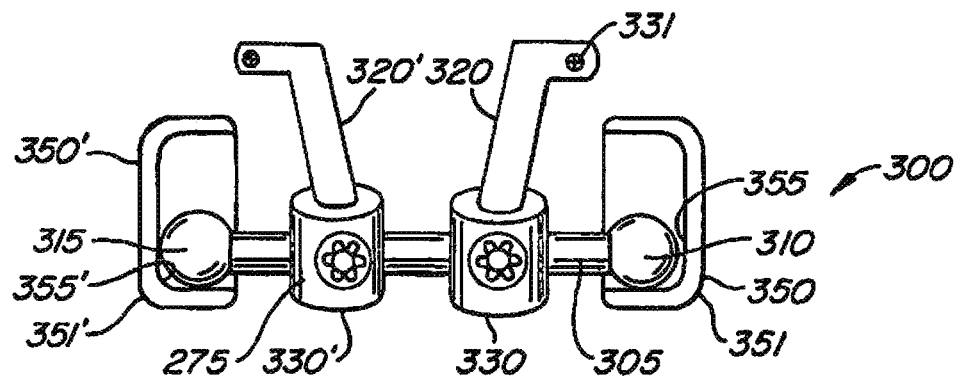
FIGS. 8A-C are views of another embodiment of an adjacent level facet arthroplasty device.

FIG. 8A is a posterior view of an anchorable facet replacement device 300 according to an alternate embodiment of the present invention. The device 300 includes a crossbar 305, a pair of cephalad arms 320, 320' and a pair of cephalad connectors 330, 330'. In this exemplary embodiment, the facets 30 and 31 of the vertebral body are replaced by the cooperative operation of the crossbar 305, the cephalad arms 320, 320' and the adaptable crossbar mounts 275 that join the cephalad arms 320, 320' to the crossbar 305 join the device to an implant, interacting with the caudal device 350. The components of the caudal implantable device 300 are designed to provide appropriate configurability and adaptability for the given disease state, patient specific anatomy and spinal level where the implant occurs.

The crossbar 305 has a first end 310 and a second end 315. The crossbar 305 can be formed from a two piece bar where the first end 310 is attached to a threaded male portion having threads (not shown). The crossbar second end 315 can be attached to a threaded female portion sized to receive the threads. It is contemplated that the threaded ends allow for the width of the crossbar to be adjusted to mate with the width between caudal bearings 350. Additional alternative embodiments of the crossbar 305 could include a series of solid crossbars of varying widths and/or thicknesses, or an adjustable crossbar having some form of locking or biasing mechanism (such as a spring-loaded tensioner or detent mechanism, etc.), as would be appreciated by those of skill in the art. Further, in an alternative embodiment, the end 310 can be configured to have a threaded male portion (instead of female portion) that fits within a female threaded portion of the crossbar 305 without departing from the scope of the invention.

A pair of caudal bearing elements 350 are also illustrated in the exemplary embodiment of the configurable and adaptable device 300 of the present invention. Each of the caudal bearing elements 350 includes a caudal cup 351 and a fixation element 360. The caudal cup 351 includes a surface 355 adapted to receive a crossbar end and a surface to engage the caudal stem head engaging surface. The fixation element 360 includes a caudal stem 365 and a distal tip 370. Alternatively, the distal tip 370 can be formed integrally with the caudal stem 365, of the same or a different material as the caudal stem 365. The caudal stem 365 and distal tip 370 can be threaded or otherwise configured to engage.

Cephalad connectors 330, 330' are provided to connect the implantable device 300 to the rods 110, 100' of the spinal implant 100 below the connection mechanism 115. The clamping mechanism 330 can attach to various portions of the spinal implant 100, including the rods 110, 100' or the connection mechanism 115. Other devices can be provided that are attached to all or part of the spinal implant 100, including cross-connectors and/or lateral rod connectors (not shown), or combinations thereof. The clamping mechanisms 330, 330' can further be adapted to lock onto the spinal implant 100 by providing an additional connection mechanism 331 such as a bolt or a screw.

Figure 8B:
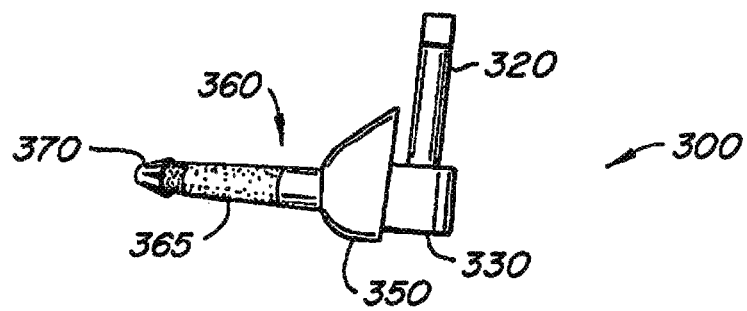
Figure 8C:
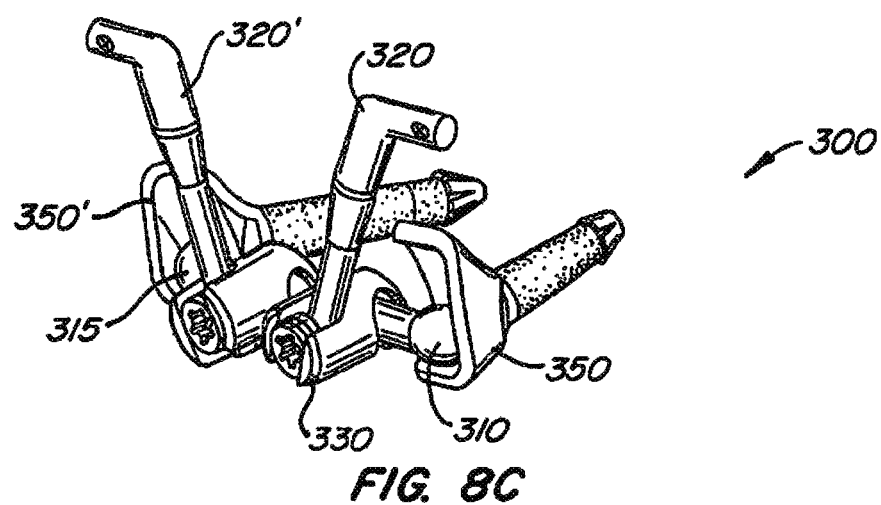

FIG. 8B illustrates the implantable device 300 from a side view; FIG. 8C illustrates the device 300 from a perspective view. Similar to the modifications described above with respect to FIG. 7, as will be appreciated by those of skill in the art, in some instances, the device can be configured to provide a single caudal arm, thus providing a 3-point fixation mechanism that, in turn, is connected to the spinal fusion device. Where a 3-point fixation design is used, the caudal arm 320 can be coupled to the cross-bar 305 such that the length of the arm 320 from the spinal fusion engaging end to the cross-bar engaging end 340 crosses the midline of the vertebra along the vertical length of the sagittal 54 plane.

Figure 8D:
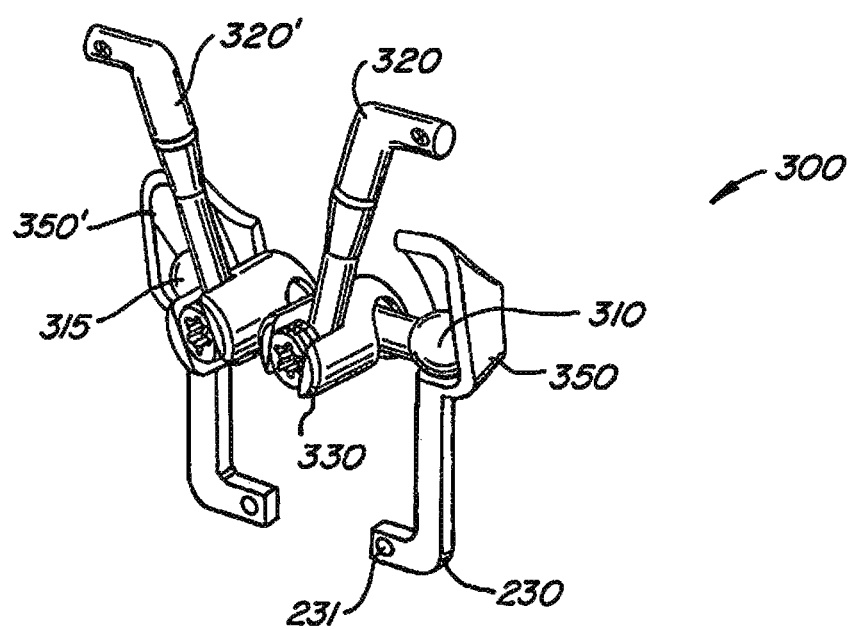
FIG. 8D illustrates yet another embodiment.

FIG. 8D illustrates an implantable device 300 suitable for use in a fusion system wherein the fusion system is being converted mid-length to provide for motion at a target joint. The device 301 has a cross-bar 305 which engages two caudal cups 350 on either end. Caudal arms 320, 320 are provided to connect the device to a spinal fixation device (such as device 100). Cephalad connectors 230, 230' are provided to connect the device to a second spinal fixation device. This, the implantable device 301 provides an articulable device between two implanted devices that stabilize the spine both in the caudal and cephalad direction. Either of the caudal arms 320, 320' or the cephalad connectors 230, 230' can be configured to engage the spinal fusion device 100 along the rod 110, the anchors 120 or the attachment mechanisms 115. Configurations can include, providing an aperture to receive, for example, a screw which engages the fusion device 100, or configuring the arm 320, 320' or connector 230, 230' to hook around the fusion device, e.g., around the rod.

Figure 9A:
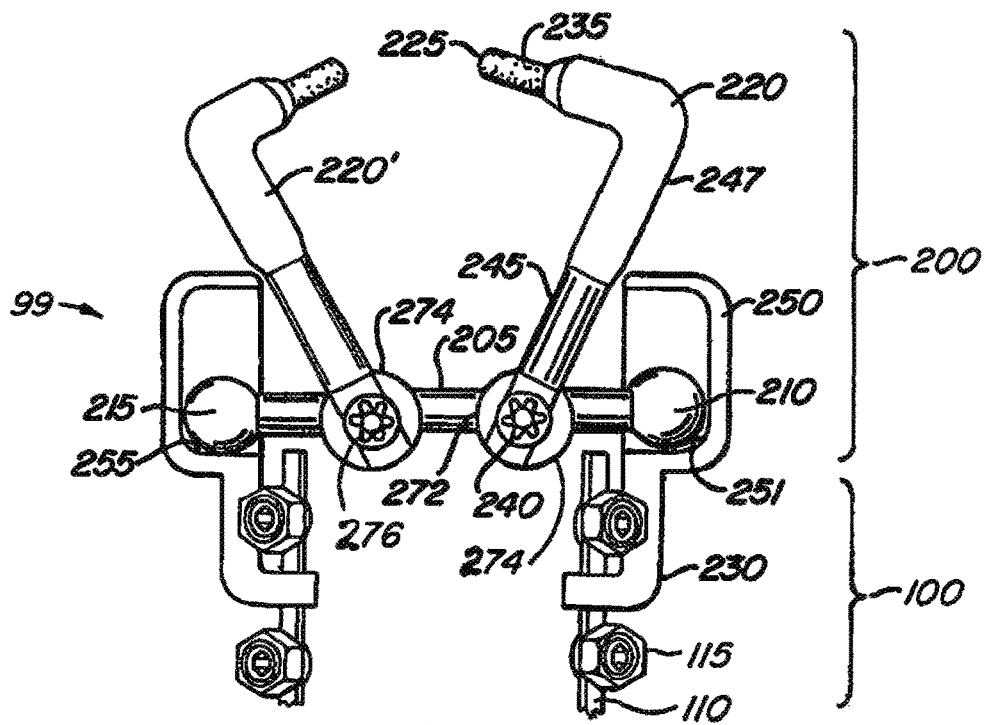
FIG. 9A is a dorsal view of the embodiment of FIG. 7A connected to a spinal fusion device.
Figure 9B:
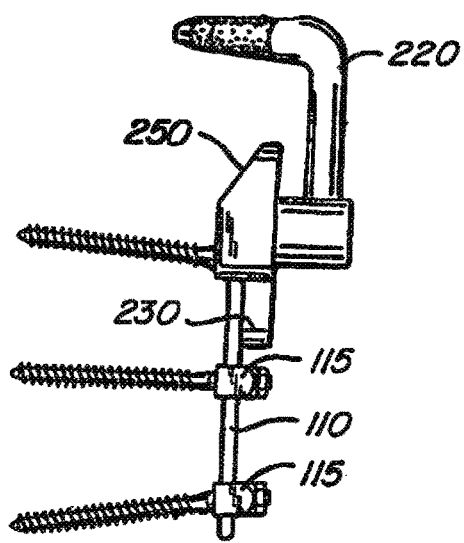
FIG. 9B is a side view of the device of FIG. 9B.
Figure 9C:
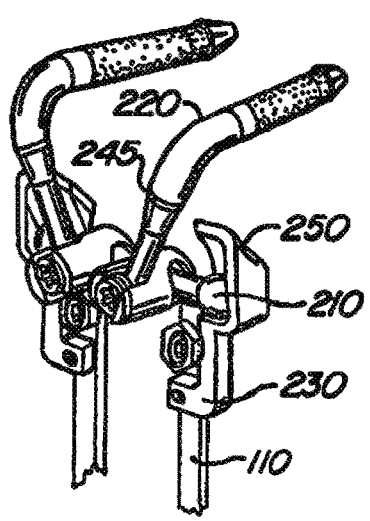
FIG. 9C is a perspective view of the device.
Figure 10A:
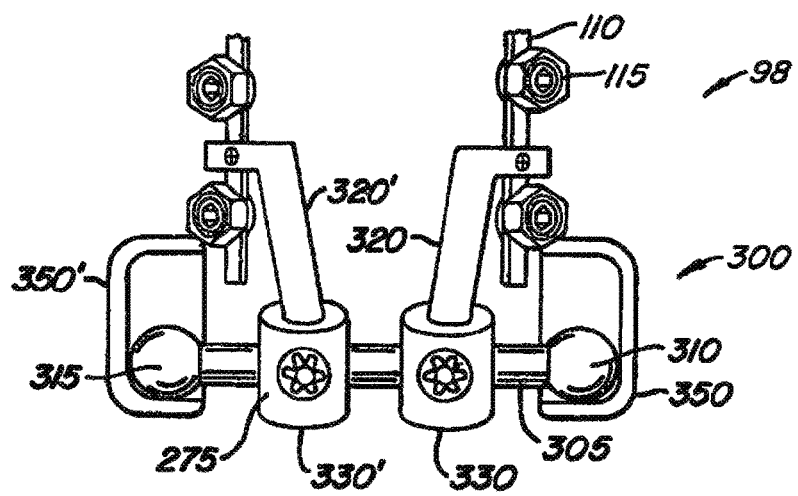
FIG. 10A is a dorsal view of the embodiment of FIG. 8A connected to a spinal fusion device.
Figure 10B:
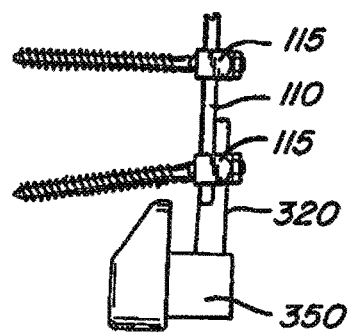
FIG. 10B is a side view of the device of FIG. 8B.
Figure 10C:
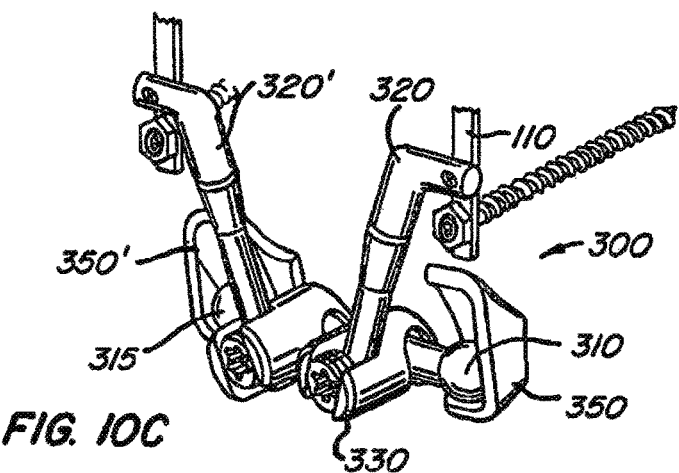
FIG. 10C is a perspective view of the device.

FIGS. 9A, 9B and 9C illustrate a spinal fusion implant 100 and facet replacement device 200 (see FIG. 7A) implanted on a portion of a spine 10. The spinal fusion implant 100 has been depicted at an angle relative to the facet replacement device 200. However, as will be appreciated by those skilled in the art, the orientation of the spinal fusion implant 100 and the facet replacement device 200 can be varied, as desired. For purposes of illustration the anchoring mechanism of the spinal fusion implant 100 have not been depicted in each depiction to avoid obscuring the invention. The design of the device 200 is such that it can be implanted during an open surgical procedure, or can be implanted through less-invasive and/or minimally-invasive means. In a desirable embodiment, the various components of the device 100 can be delivered percutaneously. Moreover while various components described can be implanted into the pedicles, these components, and variations thereof, can be implanted or secured to the pedicles, the lamina, the vertebral body, or combinations thereof. FIGS. 10A, 10B and 10C illustrate an alternative system 98 for achieving spine stabilization and facet function restoration.

Figure 11A:
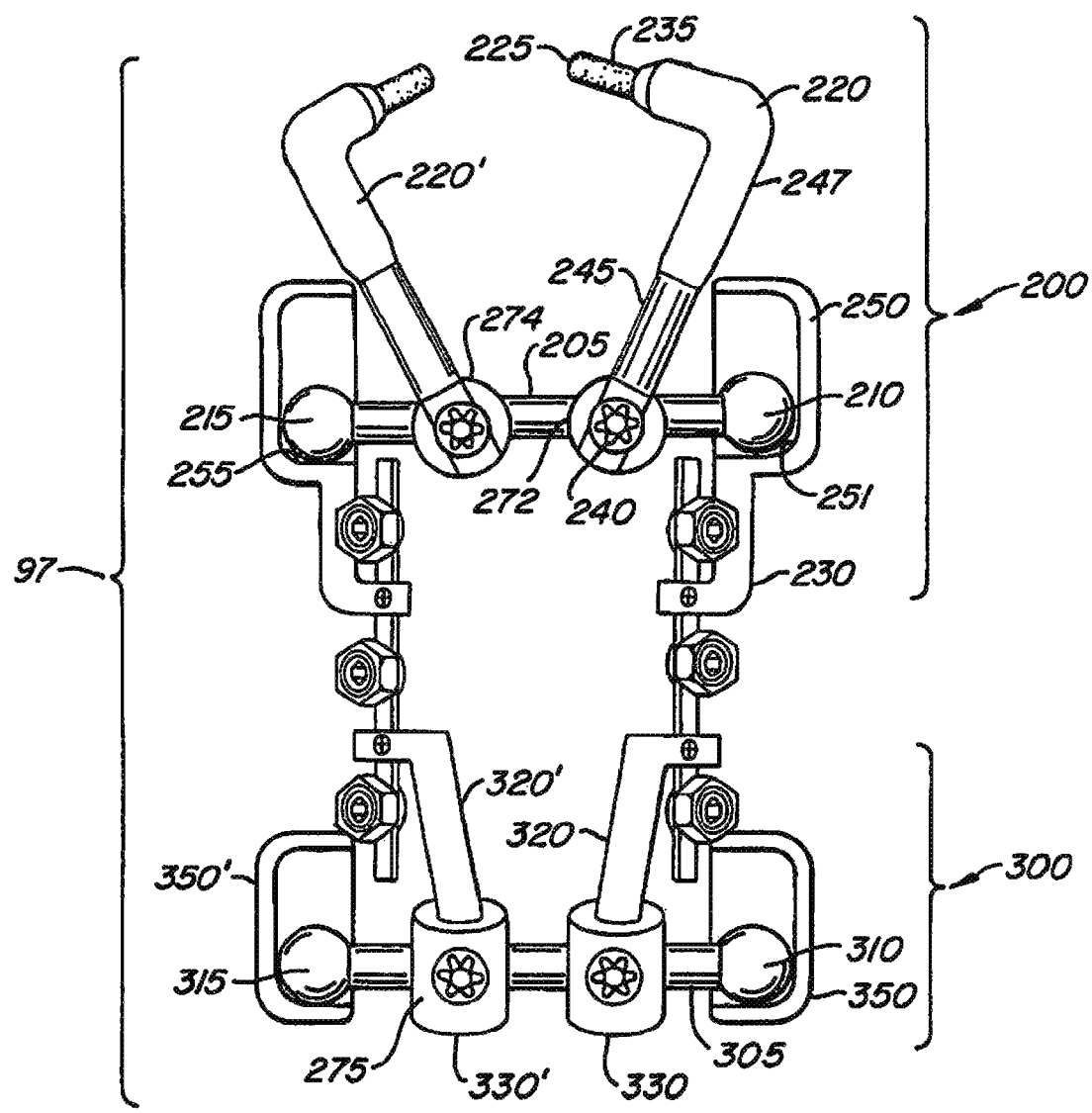
FIG. 11A is a dorsal view of another embodiment of a facet replacement system where the devices are implanted in combination with a spinal fixation system.
Figures 11B, 11C:
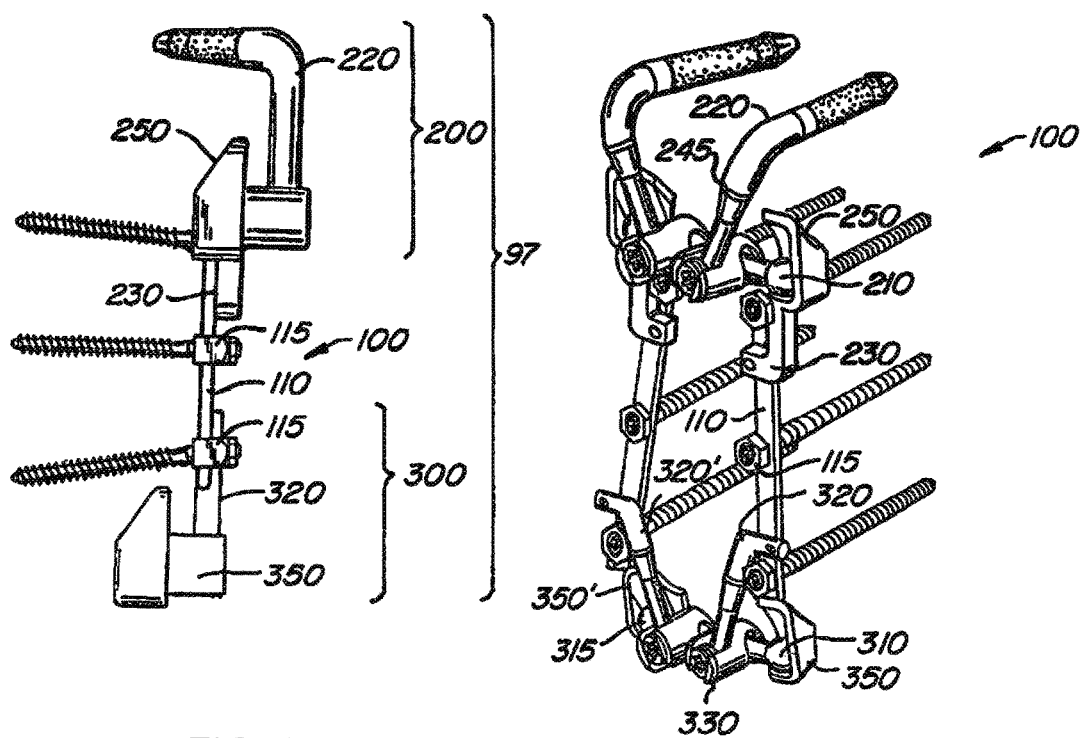
FIG. 11B is a side view of the device installed.
FIG. 11C is a perspective view of the device installed.

FIG. 11A illustrates an implanted system 97 from the dorsal view. Two or more vertebra are stabilized with a spinal fusion implant 100 and the facet joint to the next adjacent cephalad vertebra is partially or completely replaced by a device 200 while the facet joint to the next adjacent caudal vertebra is partially or completely replaced by a device 300. FIG. 11B illustrates the implanted system 97 from the side view; FIG. 11C illustrates the system from a perspective view. As will be appreciated by those of skill in the art, the length of the spine stabilization system 100 employed can vary depending upon the number of vertebra to be fused. As will be appreciated by those of skill in the art, the device of FIG. 8D can also be employed in a system, such as 97, to provide a combination of fusion with articulation.

FIG. 12 illustrates various connection and attachment designs useful, in whole or in part, in embodiments of the invention. FIG. 12A illustrates a connector 400 having a bearing 402 connected to an arm 404. The connector 400 has an arm holder 406 that connects the arm 404 to a sleeve 410. The connector illustrated in FIG. 12B enables a spinal implant, such as those depicted above, to be anchored to the spine 10 by positioning a portion of the vertebral body within the hook 410. The rod 110 (shown in FIGS. 7-8) of the spinal implant can then be inserted laterally through the opening 412 defined between the lateral portion 414 of extension 416 and flange 418 of connector portion 420. The rod may then be axially displaced along the U-shaped channel 422. The fastener (not shown) can be threaded through the lateral portion 414 of extension 416 along the axial portion 424, and into threaded engagement with threads of flanges 418, 418' which cause the lower portion of fastener to engage the elongate rod 110 (FIG. 6) and press the rod 110 tightly against the bottom of the unshaped channel 422. FIG. 12C illustrates another internal fixation device suitable for use with this invention. The internal fixation device 430 attaches to a fixation rod 110, 110' and comprises a hook 432 with a screw device 434 with an axis 436. The hook 432 has an actual hook element 438 and a shackle element 440 which grips a portion of the spine. The shackle element 440 is used to fasten the fixation rod 110 and the hook 432 on each other. The shackle element 440 forms a groove with a groove bottom 442, against which the fixation rod 110, 110' rests, and two lateral walls 444, 444' following the groove bottom 442. The two lateral walls 444, 444' of the shackle element 440 are clamped together by means of the screw device having the axis 436 by means of which the fixation rod 110, 110' can be clamped in place with its area received in the shackle element 440.

Figure 12A:
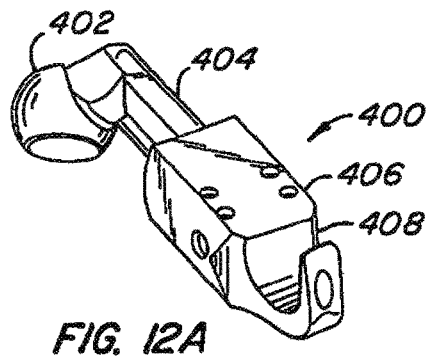
FIGS. 12A-U depict various connection and attachment systems suitable for use with the invention.
Figure 12C:
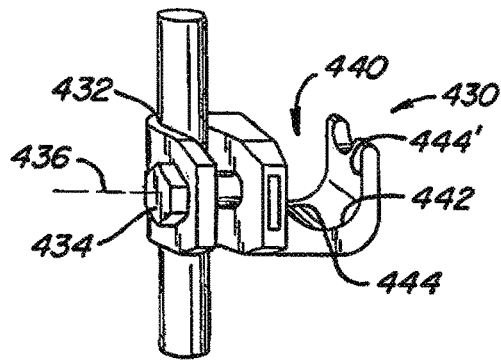
Figure 12B:
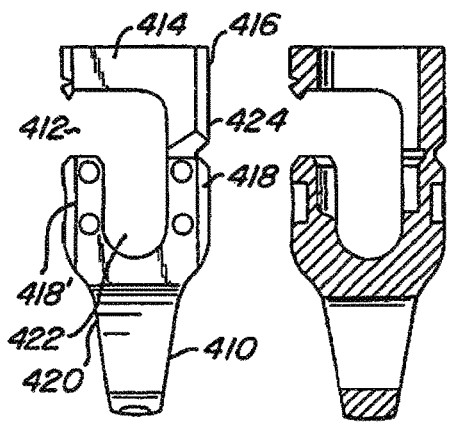
Figure 12D:
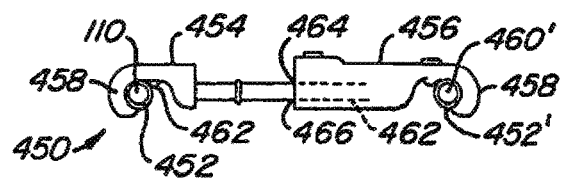

FIG. 12D illustrates a transverse connector 450 suitable for use with the present invention. The connector 450 joins two elongated spinal stabilizers 452, 452', (but which could also comprise plates), fixed to a number of vertebrae by means of anchoring members which are not shown. The transverse connector has a linking assembly having a first 454 and a second part 456 which each have an end portion terminating in a clamp 458, 458'. A variety of clamping structures could be used. They can be the same or different. For example, the clamp on one side could be closed while the clamp on the opposing side could be open. However, preferably, the clamps each include a recess 458, 458' which receive a respective rod. Setscrews 461 can be employed and received in threaded bores each terminating in a beveled area 462, 462' which biases the rod into a retaining contact with the recess. The longitudinal axis of the setscrew is offset from the longitudinal axis of the rod receiving recess so that the setscrew will bias the rod into the recess. The setscrews may include internal hexes, or other suitable torque driving means, for tightening. When they are assembled the recesses 458, 460 are both open toward a central medial line or toward each other. This arrangement can be used for initial placement of the connector on the rod 110 (FIG. 6). Thus, the connector assembly can be placed onto the rods and then tightened with respect to the length. The second member 456 of the transverse connector includes a bore 462, which receives an extension portion 464 which extends outwardly from the clamp 458 of the first part 454. The extension can move in and out of the bore 462 to contract or expand the length of the space connected and the extension 464 can rotate in the bore 462 to change the relative angle of the openings of the rod recesses of the clamps to accommodate a varying relative angle of the longitudinal axis of the rods 110. Further, the first and second members, 454, 456 can include a limit mechanism such as a flanged end on the extension 464. When employed, this flanged end is inserted into a vertical keyway 466 which is a vertical slot in the first member having an enlarged opening that is slightly larger than the diameter of the annular flange, and which will accommodate entry of the larger diameter flanged end. An undercut can be provided on either side of the keyway to allow for captured movement of the flanged end in the keyway, but allow for restriction against movement out of the keyway 466. A vertical slotted area is slightly wider than the diameter of the extension. Thus, the keyway 466 restrains the flanged end in the vertical keyway 466 as it is slid downward toward the bore 462. When the extension comes to the end of the keyway 466, it can be moved inward in the bore 462.

Figure 12E:
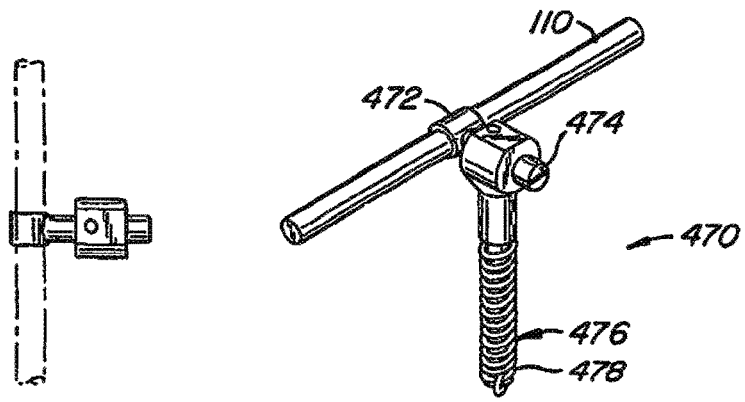

FIG. 12E illustrates a bar 110 with a threaded screw connector 470. A hollow connector 472 is provided to engage the rod 110. A fastener 474 pivotally connects the bone anchoring bolt 476, having threads 478, such that the connector 470 can attach a bar or cable 110 to a bone.

FIG. 12F illustrates a perspective view of a mounting device 480. The device 480 comprises a connector 482 with two screws 484, 484' adapted to form a screw-nut link by engaging the duct 486 of the head 488 of the connector. The connector has two vertical plane faces 490 comprising a front face and a rear face, which faces are substantially parallel and extend continuously over the full height of the connector. The connector also has two horizontal plane faces comprising a top face and a bottom face 492, 492' that are parallel to each other and substantially perpendicular to the above-mentioned vertical faces 490. The connector has a generally cylindrical duct 486 extending parallel to the front and rear faces 490, halfway between them, and perpendicular to the top and bottom faces 492, 492' through which it opens out. The connector is axially symmetrical about the axis of the duct 486. The connector has two slots 494, 494' extending generally parallel to the top and bottom faces 492, 492' in two side faces 496 of the connector that extend perpendicularly to the front and rear faces 490. Each slot 494, 494' is generally of channel section being defined by a top face 498 parallel to the top face 492 of the connector, a web face parallel to the side faces 496 of the connector, and a bottom face 498' facing the top face 498 and extending perpendicularly to the front and rear faces 490 while being slightly inclined towards the inside of the connector. The angle between the top and bottom faces 498, 498' of the slot can lie in the range 2 to 10°, for example. The slots 494, 494' co-operate with the duct 486 which extends between them to define a housing for receiving a cross-member 500, as described below. Furthermore, on either side of the axis of the duct 486, the slots 494, 494' define two junctions between which the duct 486 and the housing extend. A portion of the connector extending above the junctions forms a head 502. The two side faces 496 on the head 502 are shaped like two sectors of a common cylinder that is coaxial with the duct 486. The connector has a bottom cylindrical face 504 contiguous with the bottom face 498 of the connector, perpendicular to the duct 486, and halfway between the two side faces 496. Between them, the slots 494, 494' and the cylindrical face 504 define two jaws 506, 506' each connected to the head 502 by the two junctions. On each junction, the connector has a notch 508 extending away from the jaws 506, 506' towards the head 502. The diameter of the duct 486 is smaller in the head 502 than in the remainder of the connector. Inside the head 502, the duct 486 has a thread.

It has two screws 484 each adapted to form a screw-nut link by engaging in the duct 486 of the head 502 of a respective connector. Each screw 484 has a hexagonal socket 510 for receiving a hexagonal key for turning the screw 484 received in the duct 486. The device has two rectilinear longitudinal rods 512, 512' for extending along the backbone of a patient, each being fixed to the vertebrae by anchor members using techniques known in the art. The two rods 512, 512' typically have a circular profile as illustrated with a diameter the same as the cylindrical face 504 between the jaws. The jaws 506, 506' are adapted to make surface-on-surface contact with the rod. The cylindrical faces 504 of the jaws together extend over a circular arc of total extent exceeding 180° and selected as a function of the properties of the material of the connector so as to enable the jaws 506, 506' to be engaged on the rod 512, 512' by being snap-fastened thereon. The cylindrical faces 504 of the jaws present a geometrical outline which extends beyond the bottom face 492' of the connector 482. Thus, when the rod 512, 512' is engaged between the jaws 506, 506', the rod projects beyond the jaws in a radial direction. Finally, the device has a rectilinear cross-member 514 of generally rectangular section adapted to be received in the housings, passing right through the connectors 482.

FIG. 12G illustrates another connection system 520. A rod 110 is received through aperture 522 in a pivotal head 524 attached to an anchoring dowel 526 for anchoring the device 520 to the bone.

In FIG. 12H, the positioning and locking device 530 is made up of an upper jaw member 532 and a lower jaw member 534 having opened faces which are machined with assembly notches 536 to allow one to be positioned and pivoted against the other, leaving an opening 538 at the opposite end. A bushing, or hollow shaft, 540 passes through the two jaws 532, 534 at right angles and then through the opposite end of the jaws, with respect to the gripping jaw opening. Bushing 540, at its upper part 542, has the shape of a cone frustum with slots 544 which start from this upper part 542 and run in the direction of the axis of the bushing to end about halfway down the length thereof. The lower part of bushing 540 is threaded at 546 and is screwed into a nut 548 which clamps the two jaws 532, 534 together. A spring in the form of a staple 550 or bent wire is housed inside holes 552 each made in each one of the jaws 532, 534 also on the opposite side to the opening of the gripping jaw. Upper jaw 532 has a conical recess in its upper part and a cylindrical bore to accommodate bushing 540 and lower jaw 534 has a bore which has two opposed flat surfaces to play a part in holding bushing 540 in place especially against rotation, these flat surfaces not being depicted in the drawing. Bushing 540 can have a smaller diameter in its threaded lower part 546 and in its central part has two opposed flat surfaces, not shown in the drawing, which engage the flats on lower jaw 534 to prevent bushing 540 from rotating relative to the jaws and allow the nut to be locked. Between bushing 540 and the bores of jaw 534, 536 there is a clearance that allows the jaws device 530 to be pivoted outwardly against the face of staple spring 550, prior to the tightening operation. The clearance allows the jaws 532, 534 to be parted just enough for clipping an element between the faces of each jaw, for example, onto a rod or a hoop along which device 530 can slide and therefore change position. A rod 110 may be inserted into bushing 540 and locked in position by the clamping action of the conical position of the upper part of bushing 540 which deforms inwardly as nut 548 is tightened pulling the bushing downwardly into the conical recess of upper jaw 532. This causes upper part of bushing 540 to deform inwardly in the area of slots 544. This rod 110 may remain fixed in a concrete assembly position so that one can adjust the relative positions of all the elements of the device prior to the final operation of tightening the assembly.

FIG. 12I is a perspective view of the constructed clamp 550 with a small cut-away to show the junction between the pin connector 552 and the connecting rod 110. Tightening the bolt 554 draws the pin 556 against the distal outer surface 558 of the clamp body 560. This action braces the pin against the clamp preventing the rotation of the pin connector 552 and thus the pin 556. Moreover, the pin 556 is prevented from moving axially with respect to connector 552. Tightening the bolt 554 additionally draws the rod-engaging surface 580 of the connector 552 into engagement with the connecting rod 110. This interference has a number of effects that further prohibit any movement of the tightened clamp 550. First, friction between the rod-engaging surface 580 and the outer surface of the rod 110 further prevents any rotation of the pin connector 552. Additionally, the force exerted by the pin connector at this junction pushes the rod 110 in the direction of arrow b. This ensures that the rod 110 is seated against the back wall 582 of the slot 584 providing a good rigid mechanical junction between the connecting rod 110 and the clamp body 560 preventing rotation of the clamp body around or sliding along the connecting rod 110. The clamp body 560 does not substantially squeeze-down on or close over the connecting rod when the bolt 554 is tightened. It is only the interference between the rod-engaging surface and the rod 110 that prevents movement between the rod 110 and clamp 550.

FIG. 12J illustrates an attachment mechanism 570 has a threaded nut 572 having female threads 574 for engaging the shaft 576 of an anchoring shaft 578. The threaded nut 572 has a clamp 580 for engaging a rod 110. The clamp 580 forms an adjustable aperture 582. The aperture 582 is adjusted by tightening a fastener 584.

FIG. 12K illustrates a bone bolt 590 suitable for use with the invention. Bone bolt 590 is shown attached to a clamp 592 with the longitudinal axis L1, and clamp 592 is shown attached to a spinal implant rod 594 with a longitudinal axis L2. Clamp 592 includes a clamp bolt 596, an arm 598, a rod interface washer 600, a set screw 602, and a nut 604. Clamp bolt 596 has an aperture 606 for receiving rod 594, and while the aperture is shown closed around rod 594, it will nevertheless be understood that an open-sided aperture may also be used to permit top-loading of rod 594 into clamp 592. Set screw 602 is inserted through a threaded opening 608 and into aperture 606 in clamp bolt 596 so as to allow set screw 602 to push against rod 594. Arm 598 has a bore 610 for receiving bone bolt 590. Arm 598 is simultaneously tightened to clamp 592 when set screw 602 is tightened against rod 594. As set screw 602 pushes against rod 594, rod 594 pushes against rod interface washer 600, which pinches arm 598 between rod interface washer 600 and stop 612. In this manner, set screw 602 acts as a compression member to tighten clamp 592 and achieve substantial fixation of arm 598 to rod 594.

FIG. 12L depicts fasteners 620 suitable for use in the invention. The fastener 620 has an aperture 622 for receiving a rod 110 (not shown) and is adopted to allow the diameter of the aperture 622 to increase and decrease in order to facilitate engaging the rod 110. A bolt 624 is provided to communicate through a second aperture 626 to decrease the aperture 622 that received the rod.

FIG. 12M retainer assembly 630 includes a set screw 632 and a generally rectangular retainer block 634 into which angular member 636 and rod 110 extend. Block 634 has a rod passage 638 which receives rod 110. Rod 110 (not shown) can have a substantially circular cross-section; however, rods having various other cross-sections, such as hexagonal or oval cross-sections, could be used with corresponding modifications to rod passage 638. Block 634 also includes a transverse passage 640 which receives inner end portion 642 of angular member 636 and communicates with rod passage 638. Transverse passage 640 includes a plurality of mating surfaces 644 which engage similarly shaped retaining surfaces or teeth 646 that project radially outwardly from inner end portion 642 of angular member 636. Meshing engagement between mating surfaces 644 on block 634 and teeth 648 on inner end portion 642 prevents rotational movement of angular member 636 about a longitudinal central axis 650 of inner end portion 642. It is understood that mating surfaces of various shapes may be formed in transverse passage 640 to receive similarly shaped retaining surfaces formed on block 634.

FIG. 12N illustrates another attachment mechanism 660. Pincers 662 attached to the vertebras, formed by two curved claws with opposite concavities, one of which 664 forms part of the body 666 of the pincer and the other 668 independent, with a cylindrical lateral prolongation 610 which on passing tightly through the body 666 of the pincer allows it to make axial or turning displacements to adapt the relative position of the two claws to the shape and sizes of the zone of the vertebra where it is fastened. There is a prisoner screw 670 for immobilization of the movable claw 668 in the suitable position, as well as another prisoner screw 672 to retain insertion of the connecting prolongation 674 of the pincer-bar connectors 676 tautening wire 678 through-orifice 679 for lateral displacement of the vertebras.

FIG. 12O illustrates yet another attachment mechanism 680. A crossbar 682 is provided with a clamping mechanism 684 having a sizable aperture 686. The sizable aperture 686 is adjustable by adjusting screw 688. The aperture 686 is configured to, for example, receive a rod 110.

FIG. 12P illustrates an alternate mechanism 640. A pair of parallel rods 642, 642' are provided. The first parallel rod 642 is integrated with a connector 644 for the second parallel rod 642'. The second parallel rod 642' can be fed through an aperture 646 on the connector 644. A nut 648 is provided to secure the second nut 642' in the aperture 646.

FIG. 12Q illustrates a connector 770 having a rod 110 connected to a crossbar 772. The rod is secured through an aperture 774. A nut 776 is provided to secure the rod 110.

FIG. 12R illustrates a connector assembly 780 suitable for use with the invention from a perspective view, an end view and a top view. The assembly attaches spinal implant rod 110 with a longitudinal axis L1 to the shaft of a vertebral anchor with the longitudinal axis. Connection assembly 780 includes a bolt 782, a clevis 784, a rod interface washer 786, and a set screw 788. Bolt 782 has an aperture 790 for receiving a rod 110 in a spinal implant system. While a closed aperture is depicted, it will be appreciated than an open-sided aperture may also be used to permit top loading the of the connector rod. Set screw 786 is inserted through a threaded opening 792 in bolt 786 and into aperture 790 to allow set screw 786 to push against rod A. Clevis 784 is a u-shaped piece with a bore 794 for receiving a vertebral anchor or bolt B and is simultaneously tightened when set screw 788 is tightened against rod A. The shaft B may be roughened and the interior of clevis 784 may be correspondingly roughened to increase friction between the pieces. As set screw 788 pushes against rod A, rod A pushes against rod interface washer 786. This force pinches the ends 796 and 798 of clevis 784 together between rod interface washer 786 and stop 800, which tightens clevis 784 together between rod interface washer 786 and stop 790.

FIG. 12S depicts a multiaxial connector 700 suitable for the invention. The connector 700 has a first connecting element 702 perforated with a bore 704 designed to receive the second threaded part 706 of the fixing screw 708, another bore 710 comprising in its inner part an annular track 712 with spherical profile and a slot 714 passing through the bore 704 to emerge inside the bore 710 at the annular track 716, a second connecting element 718 perforated with a bore 720 designed to receive the lining rod 722 of a threaded hole 724 co-operating with a clamping screw 726 for locking the rod in translation and linking means 728 forming a ball joint enabling the first and second elements to be coupled together such that the elements can pivot relative to each other to present the linking rod 729 in specific angular positions and to laterally offset the linking rod relative to the pivoting centre of the elements.

FIG. 12T illustrates a connection assembly 730 having a longitudinal member 732 and a housing 734. Longitudinal member 732 has an aperture 736 for receiving a rod 110, for example in a spinal system. Open sided apertures can be used to permit top loading of the rod. A threaded opening 738 is provided to communicate with a set screw 740. The housing 734 has a passageway 742 for receiving a shaft or shank of a vertebral anchor.

FIG. 12U illustrates a connection assembly 750 used with an offset connector or spindle. The assembly 750 has aperture threaded bolt 752 for connection to bone. The fence bolt 752 fits within an aperture 754 of an anchor 756. A cross member 758 connects the anchor 756 to a rod holder 760. A rod 110 fits within an aperture 762 of the rod holder. A set screw 764 is provided to fix the location of the rod in the aperture. A second set screw 766 is provided to fix the location of the fence bolt 752 within the aperture 754 of anchor 756.

A variety of connectors that would be suitable for use in the invention include, for example, those described in U.S. Pat. Nos. 6,231,575, 6,309,391, 6,340,361, 6,342,054, 6,368,320, 6,749,361; U.S. Patent Publication Nos. 2002/0049446, 2002/0042613, 2002/0013585, 2002/0013588, 2002/0082601; European Patent Nos. 1205152, 1103226; PCT Patent Publication Nos. WO 01/30248, WO 02/34150, WO 01/67972, WO 02/02024, WO 01/06939, WO 02/24149.

Figure 13:
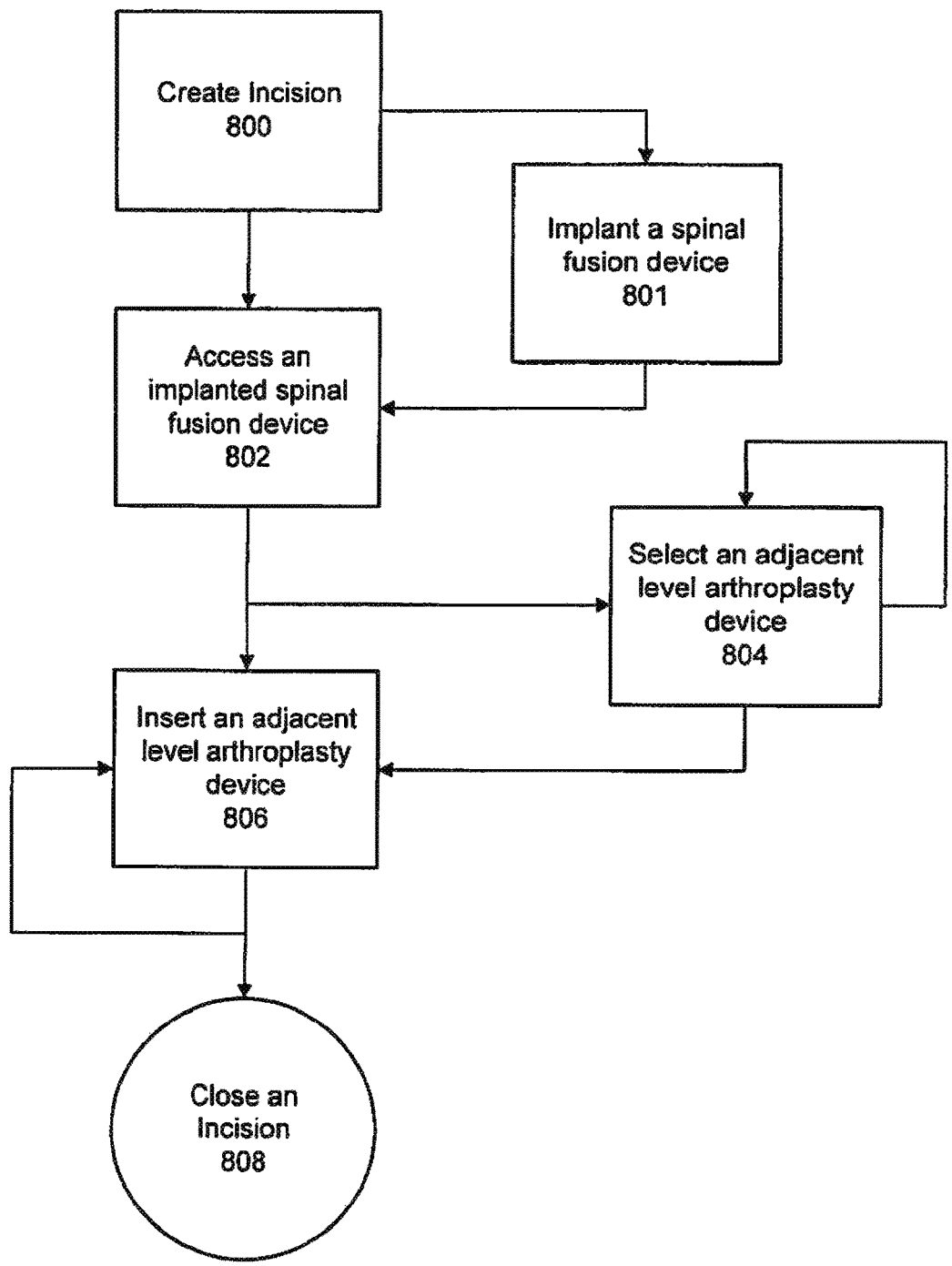
FIG. 13 is a flow chart of a method according to the invention.

Turning now to FIG. 13, a flow chart depicting a method is depicted. Initially, an incision is created 800 to access a target location of the spine. As will be appreciated, this devices of this application can be implanted concurrently with the implantation of a spinal fusion device, such as a rod and screw, or in a subsequent procedure. If the devices are implanted concurrently with the fusion device, then the physician would proceed with first implanting the spinal fusion device 801. Alternatively, where the fusion device has already been implanted (e.g., where this procedure revises the prior surgical procedure), then the physician accesses the implanted fusion device 802 immediately following creating the incision 800. Thereafter, the physician can select one or more adjacent level arthroplasty devices 804 to use with the implanted spinal fusion device. Once the devices are selected 804, the devices are then implanted 806. As will be appreciated by those of skill in the art, due to the modularity of the designs employed, it is possible for the physician to choose a first adjacent level arthroplasty device, implant it in conjunction with the spinal fusion device and then select a different device based on, for example, experience or in situ appearance of the suitability of the device. Additionally, adjustments to the connection of the adjacent level arthroplasty device can be made without departing from the scope of the invention. Once the physician is satisfied with the selection, the incision is then closed 808.

Figure 14:
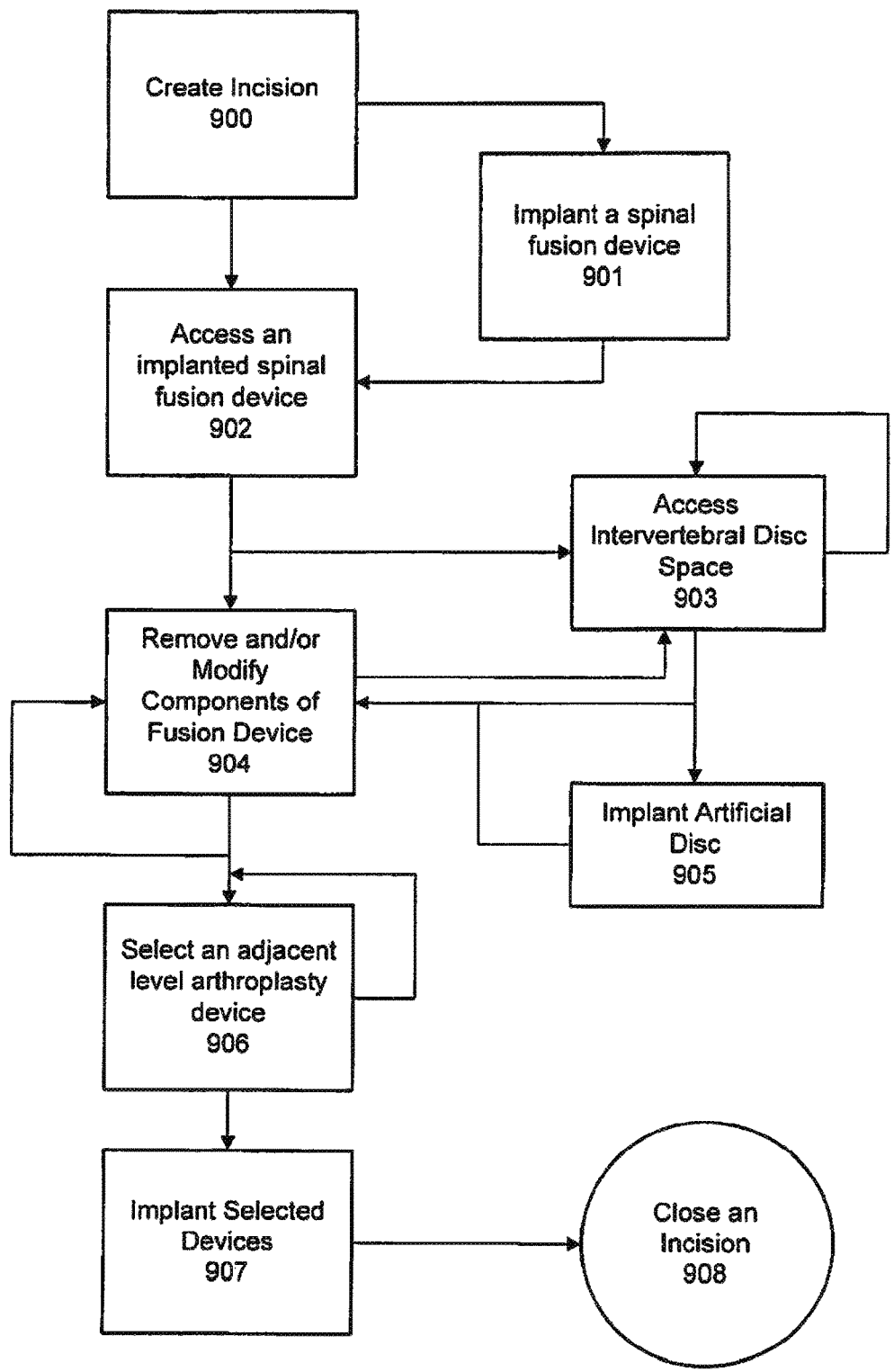
FIG. 14 is a flow chart of another method according to the invention.

FIG. 14 depicts the flow chart for an alternate embodiment of a method of the present invention, particularly well suited for revision of an already-fused functional spinal unit, to partial or full natural motion. Initially, an incision is created 900 to access a target location of the spine. The spinal fusion device can be implanted 901 at that time or during a previous procedure. As discussed, this procedure is well suited for a subsequent procedure. The physician then exposes at least a portion of the spinal fusion instrumentation 902. Thereafter, the physician can remove and/or modify the components of the existing spinal fusion instrumentation. Removal and/or modification includes the resecting of individual fusion components, such as rods. If necessary, the physician can access the intervertebral disk space 903 to separate any arthrodesis across the disk space as well as remove any fusion cages and/or other associated intervertebral fusion devices (including intervertebral spacer and/or dynamic stabilization devices) 904. If desired, the physician can implant an artificial disk or nucleus replacement 905. The physician can select one or more adjacent level arthroplasty devices 906 to use with the remaining components of the spinal fusion instrumentation. Once the devices are selected 906, the devices are then implanted 907.

As will be appreciated by those of skill in the art, due to the modularity of the designs employed, it is possible for the physician to choose a first adjacent level arthroplasty device, implant it in conjunction with the spinal fusion device and then select a different device based on, for example, experience or in situ appearance of the suitability of the device. Additionally, adjustments to the connection of the adjacent level arthroplasty device can be made without departing from the scope of the invention. Once the physician is satisfied with the selection, the incision is then closed 908. It should also be appreciated that the present method could be used to revise the fusion of a single functional spinal unit, or could be used in any portion or location of a spinal fusion spanning multiple spinal levels.

Though the present invention has been described with respect to several embodiments, those skilled in the art will recognize that the invention is capable of alternate embodiments within the scope of the appended claims.

What is claimed is:

1. An implantable facet arthroplasty device for association with a first vertebra and a second vertebra comprising:
    (a) a crossbar;
    (b) a spinal fusion device;
    (c) a first component having a first attachment mechanism adapted to attach to a first location of the spinal fusion device attached to a first vertebra and a second attachment mechanism adapted to engage the crossbar;
    (d) a second component having a second attachment mechanism adapted to attach to a second location of the spinal fusion device attached to the first vertebra and a second attachment mechanism adapted to engage the crossbar;
    (e) a caudal bearing element having a caudal cup and fixation element, wherein the caudal cup is configured to engage the crossbar and the fixation element is configured to engage a vertebral body;
    wherein the spinal fusion device comprises a pair of elongated members configured to extend along a portion of the spine adjacent a cephalad vertebra and a caudal vertebra and a plurality of attachment mechanisms for mounting the spinal fusion device to the cephalad vertebra and the caudal vertebra, and
    wherein the first component articulates relative to the second component and when the facet arthroplasty device is implanted the first vertebra articulates relative to the facet arthroplasty device.

2. The implantable facet arthroplasty device of claim 1, wherein the fixation device comprises a caudal stem.

3. The implantable facet arthroplasty device of claim 2, wherein the fixation device comprises a distal tip.

4. The implantable facet arthroplasty device of claim 3, wherein the caudal stem is configured to engage the distal tip.

5. An implantable adjacent level arthroplasty device for implantation between a first vertebra and a second vertebra having a vertebra engaging a fusion device comprising:
    (a) a crossbar having a first end;
    (b) a spinal fusion device;
    (c) a first component having a first attachment mechanism adapted to attach to a first location of the spinal fusion device attached to a first vertebra and a second attachment mechanism adapted to attach to the crossbar; and
    (d) a second component having a second attachment mechanism adapted to attach to the second location of a spinal fusion device attached to the first vertebra and a second attachment mechanism adapted to attach to the crossbar;
    (e) a caudal bearing element having a caudal cup and fixation element, wherein the caudal cup is configured to engage the first end of the crossbar and the fixation element is configured to engage a vertebral body;
    wherein the spinal fusion device comprises a pair of elongated members configured to extend along a portion of the spine adjacent a cephalad vertebra and a caudal vertebra and a plurality of attachment mechanisms for mounting the spinal fusion device to the cephalad vertebra and the caudal vertebra, and
    wherein the first component articulates relative to the second component and when the facet arthroplasty device is implanted the first vertebra articulates relative to the facet arthroplasty device.

* * * * *